United States Patent
Chen et al.

(10) Patent No.: US 12,339,213 B2
(45) Date of Patent: Jun. 24, 2025

(54) METHOD FOR CLASSIFYING AND COUNTING WHITE BLOOD CELLS, HEMATOLOGY ANALYZER, AND COMPUTER READABLE STORAGE MEDIUM

(71) Applicant: Shenzhen Mindray Animal Medical Technology Co., Ltd., Shenzhen (CN)

(72) Inventors: Pengzhen Chen, Shenzhen (CN); Fangang Kong, Shenzhen (CN)

(73) Assignee: Shenzhen Mindray Animal Medical Technology Co., Ltd., Shenzhen (CN)

( * ) Notice: Subject to any disclaimer, the term of this patent is extended or adjusted under 35 U.S.C. 154(b) by 524 days.

(21) Appl. No.: 17/555,347

(22) Filed: Dec. 17, 2021

(65) Prior Publication Data

US 2022/0113238 A1     Apr. 14, 2022

Related U.S. Application Data

(63) Continuation of application No. PCT/CN2019/091932, filed on Jun. 19, 2019.

(51) Int. Cl.
*G01N 15/10*     (2024.01)
*G01N 33/49*     (2006.01)

(52) U.S. Cl.
CPC ........... *G01N 15/10* (2013.01); *G01N 33/491* (2013.01); *G01N 2015/1024* (2024.01)

(58) Field of Classification Search
CPC .......... G01N 15/10; G01N 33/491; G01N 2015/1024; G01N 2015/016; G01N 2015/1006; G01N 15/1031; G01N 33/49; G01N 35/00

See application file for complete search history.

(56) References Cited

U.S. PATENT DOCUMENTS

| | | | |
|---|---|---|---|
| 5,389,549 A | 2/1995 | Hamaguchi et al. | |
| 11,193,927 B2* | 12/2021 | Li | G06V 20/698 |
| 2011/0053210 A1* | 3/2011 | Matsumoto | G01N 33/49 |
| | | | 435/288.7 |

FOREIGN PATENT DOCUMENTS

| | | |
|---|---|---|
| CN | 101266205 A | 9/2008 |
| CN | 101464245 A | 6/2009 |
| CN | 101470109 A | 7/2009 |
| CN | 104297497 A | 1/2015 |

(Continued)

*Primary Examiner* — Brian J. Sines
(74) *Attorney, Agent, or Firm* — Kory D. Christensen

(57) ABSTRACT

The disclosure provides white blood cell classifying and counting method, blood analyzer, and computer readable storage medium. The method includes: obtaining a first histogram of white blood cells in a blood sample treated by a first hemolytic agent and a second histogram of white blood cells in the blood sample treated by a second hemolytic agent, wherein a ghost value in the second histogram is smaller than a ghost value in the first histogram, and the ghost value in the second histogram is smaller than a threshold value; determining peak type of the second histogram; when the peak type is double-peak, performing classification and counting of white blood cells using the second histogram; and when the peak type is single-peak, performing classification and counting of white blood cells by combining a classification result and a counting result of the second histogram and a classification result of the first histogram.

19 Claims, 11 Drawing Sheets

(56) References Cited

FOREIGN PATENT DOCUMENTS

| | | |
|---|---|---|
| CN | 109270281 A | 1/2019 |
| JP | H02304354 A | 12/1990 |
| WO | 1998002727 A1 | 1/1998 |
| WO | 2018049064 A1 | 3/2018 |

* cited by examiner

METHOD FOR CLASSIFYING AND COUNTING WHITE BLOOD CELLS, HEMATOLOGY ANALYZER, AND COMPUTER READABLE STORAGE MEDIUM

CROSS-REFERENCE TO RELATED APPLICATIONS

This application is a continuation of International Application No. PCT/CN2019/091932, filed Jun. 19, 2019, the content of which is incorporated herein by reference.

TECHNICAL FIELD

The present disclosure generally relates to the technical field of hematological analysis, and more specifically to a method for classifying and counting white blood cells, a hematology analyzer, and a computer-readable storage medium.

BACKGROUND

At present, an impedance method is commonly used for counting and classifying white blood cells of animals. Clinically, the counting and classification of white blood cells in animals are of great significance to the diagnosis and treatment of animals. During the counting and classification of white blood cells in animals using an impedance method, the counting and classification are performed only once after a leukocytic reaction. Such a method still has some shortcomings. The root cause lies in the particularity of blood cells in animals, such as differences in shape and volume, and different impact of ambient temperature, reagents, and intensity of reaction. For example, under a certain condition, after a specific amount of hemolytic agent is used to react with a human blood sample, a white blood cell volume histogram generated by collected signals is less affected by ghosts (red blood cell fragments, PLTs, etc.), and various particle populations are distributed away from each other on the histogram, so that the counting and classification of white blood cells can be achieved accurately.

However, a white blood cell histogram generated after the reaction of an animal blood sample can hardly achieve both accurate counting and classification. If a small amount of hemolytic agent is used, lymphocytic particles that are relatively small in volume in a generated animal white blood cell histogram will be severely interfered by ghosts, and it is thus difficult to implement accurate counting and classification of white blood cells. In this case, various particle populations of white blood cells are usually distributed away from each other. If a large amount of hemolytic agent is used, lymphocytic particles that are relatively small in volume in a generated animal white blood cell histogram will be less interfered by ghosts, and it is thus possible to achieve accurate counting of white blood cells. However, various particle populations of white blood cells are often distributed close to each other, and it is thus difficult to achieve accurate classification. In addition, for the same amount of hemolytic agent, histograms generated after reactions of different animal white blood cells may differ greatly from each other. Therefore, in one-time counting and classification of white blood cells in animals using an impedance method, due to the particularity of animal blood cells and the sensitivity to external environmental conditions, there are certain challenges in the measurement of animal white blood cells.

SUMMARY

The disclosure is proposed to solve at least one of the above-mentioned problems. Specifically, an aspect of the disclosure provides a method for classifying and counting white blood cells, comprising:
  acquiring a first white blood cell histogram of white blood cells in a blood sample treated with a first hemolytic agent and a second white blood cell histogram of white blood cells in the blood sample treated with a second hemolytic agent, wherein a ghost value in the second white blood cell histogram is less than a ghost value in the first white blood cell histogram, and the ghost value in the second white blood cell histogram is less than a ghost value threshold;
  determining a peak type of the second white blood cell histogram;
  performing white blood cell classification and counting based on the second white blood cell histogram when the peak type of the second white blood cell histogram is double-peak; and
  performing white blood cell classification and counting by combining a classification result and a counting result of the second white blood cell histogram and a classification result of the first white blood cell histogram when the peak type of the second white blood cell histogram is single-peak.

Another aspect of the disclosure provides a method for classifying and counting white blood cells, the method comprising:
  acquiring a first white blood cell histogram of white blood cells in a blood sample treated with a hemolytic agent for a first treatment time and a second white blood cell histogram of white blood cells in the blood sample treated with the hemolytic agent for a second treatment time, wherein the second treatment time is longer than the first treatment time, a ghost value in the second white blood cell histogram is less than a ghost value in the first white blood cell histogram, and the ghost value in the second white blood cell histogram is less than a ghost value threshold;
  determining a peak type of the second white blood cell histogram;
  performing white blood cell classification and counting based on the second white blood cell histogram when the peak type of the second white blood cell histogram is double-peak; and
  performing white blood cell classification and counting by combining a classification result and a counting result of the second white blood cell histogram and a classification result of the first white blood cell histogram when the peak type of the second white blood cell histogram is single-peak.

Still another aspect of the disclosure provides a computer-readable storage medium comprising a program that can be executed by a processor to implement the method described above.

Yet another aspect of the disclosure provides a hematology analyzer, comprising:
  a reaction cell;
  a sampling needle assembly configured to discharge a blood sample to be analyzed to the reaction cell;
  a hemolytic agent delivery component configured to deliver a hemolytic agent to the reaction cell, the hemolytic agent comprising a first hemolytic agent and a second hemolytic agent;

a resistive detector configured to detect white blood cells in a blood sample treated with the first hemolytic agent and generate first signals, and to detect white blood cells in the blood sample treated with the second hemolytic agent and generate second signals; and a processor configured to:

acquire a first white blood cell histogram based on the first signals and acquire a second white blood cell histogram based on the second signals, wherein a ghost value in the second white blood cell histogram is less than a ghost value in the first white blood cell histogram, and the ghost value in the second white blood cell histogram is less than a ghost value threshold;

perform white blood cell classification and counting based on the second white blood cell histogram when the peak type of the second white blood cell histogram is double-peak; and perform white blood cell classification and counting by combining a classification result and a counting result of the second white blood cell histogram and a classification result of the first white blood cell histogram when the peak type of the second white blood cell histogram is single-peak.

According to the method for classifying and counting white blood cells, the hematology analyzer, and the storage medium in the embodiments of the disclosure, a first white blood cell histogram and a second white blood cell histogram of white blood cells in blood samples respectively treated with a first hemolytic agent and a second hemolytic agent are acquired, and a manner of counting and classification of white blood cells is determined according to a peak type of the second white blood cell histogram. When the peak type of the second white blood cell histogram is double-peak and a ghost value in the second white blood cell histogram is less than a ghost value threshold, ghosts hardly interfere with the counting based on the second white blood cell histogram. In addition, since the second white blood cell histogram is double-peak and regions of particle populations of various types of white blood cells in the second white blood cell histogram are distributed away from each other, accurate classification and counting results of white blood cells in blood can be obtained directly by means of counting based on the second white blood cell histogram. When the peak type of the second white blood cell histogram is single-peak, white blood cell classification and counting are performed by combining a classification result and a counting result of the second white blood cell histogram and a classification result of the first white blood cell histogram. When the peak type of the second white blood cell histogram is single-peak, particle populations of white blood cells in the second white blood cell histogram are distributed close to each other and cannot be easily classified, but the second white blood cell histogram is less affected by ghosts, and therefore the counting result of the second white blood cell histogram is more accurate than that of the first white blood cell histogram. Since the first white blood cell histogram has two peaks, particle populations of white blood cells in the first white blood cell histogram are distributed away from each other and can be easily classified. Therefore, classification and counting of white blood cells are performed by combining a classification result and a counting result of the second white blood cell histogram determined as single-peak and a classification result of the first white blood cell histogram, such that more accurate classification and counting results of white blood cells can be obtained. Therefore, the method of the embodiments of the disclosure can improve the accuracy of counting and classification of white blood cells.

BRIEF DESCRIPTION OF THE DRAWINGS

In order to illustrate the technical solution in the embodiments of the disclosure more clearly, a brief introduction to the drawings required for the embodiments will be provided below. The drawings in the following description are merely some of the embodiments of the disclosure, and those of ordinary skill in the art would also have been able to obtain other drawings according to these drawings without involving any inventive effort.

DETAILED DESCRIPTION

Figure 1:
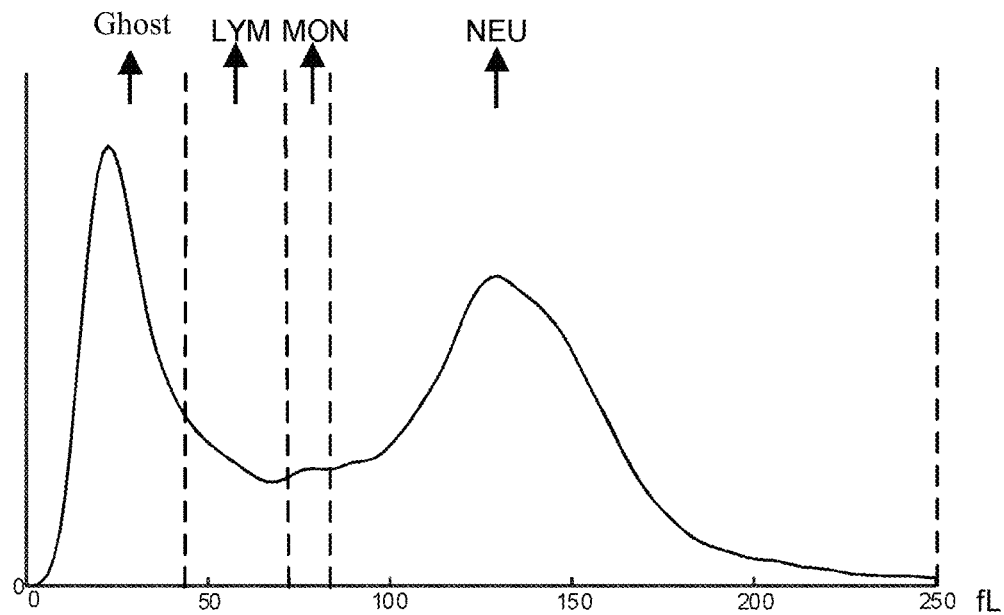
FIG. 1 is a schematic diagram of a first white blood cell histogram in one embodiment of the disclosure.

In order to make the objects, technical solutions, and advantages of the disclosure more apparent, the example embodiments according to the disclosure will be described in detail below with reference to the accompanying drawings. Apparently, the embodiments described are merely some, rather than all, of the embodiments of the disclosure. It should be understood that the disclosure is not limited by the example embodiments described herein. All other embodiments derived by those skilled in the art without creative efforts on the basis of the embodiments of the disclosure described in the disclosure shall fall within the scope of protection of the disclosure.

In the following description, a large number of specific details are given to provide a more thorough understanding of the disclosure. However, it will be understood to those skilled in the art that the disclosure can be implemented without one or more of these details. In other examples, some well-known technical features in the art are not described in order to avoid obscuring the disclosure.

It should be understood that, the disclosure can be implemented in different forms and should not be construed as being limited to the embodiments presented herein. On the contrary, these embodiments are provided to make the disclosure thorough and complete, and to fully convey the scope of the disclosure to those skilled in the art.

The terms used herein are intended only to describe specific embodiments and do not constitute a limitation to the disclosure. As used herein, the singular forms of "a", "an", and "said/the" are also intended to include plural forms, unless the context clearly indicates otherwise. It should also be appreciated that the terms "comprise" and/or "include", when used in the specification, determine the existence of described features, integers, steps, operations, elements, and/or components, but do not exclude the existence or addition of one or more other features, integers, steps, operations, elements, components, and/or groups thereof. As used herein, the term "and/or" includes any and all combinations of relevant listed items.

For a thorough understanding of the disclosure, a detailed structure will be proposed in the following description to explain the technical solutions proposed in the disclosure. The optional embodiments of the disclosure are described in detail as follows. However, the disclosure may also have other implementations in addition to these detailed descriptions.

In order to solve the technical problems that there are certain challenges in the testing of white blood cells and there is a poor accuracy due to the particularity of blood cells and the sensitivity to external environmental conditions during one-time white blood cell counting and classification in blood test, an embodiments of the disclosure provide a method for classifying and counting white blood cells, the method comprising: acquiring a first white blood cell histogram of white blood cells in a blood sample treated with a first hemolytic agent and a second white blood cell histogram of white blood cells in a blood sample treated with a second hemolytic agent, wherein a ghost value in the second white blood cell histogram is less than a ghost value in the first white blood cell histogram, and the ghost value in the second white blood cell histogram is less than a ghost value threshold; determining a peak type of the second white blood cell histogram; performing white blood cell classification and counting based on the second white blood cell histogram when the peak type of the second white blood cell histogram is double-peak; and performing white blood cell classification and counting by combining a classification result and a counting result of the second white blood cell histogram and a classification result of the first white blood cell histogram when the peak type of the second white blood cell histogram is single-peak.

According to the above-mentioned method, after two white blood cell counts under different hemolytic agents are acquired, a first white blood cell histogram and a second white blood cell histogram are generated, and a white blood cell counting and classification method is comprehensively analyzed according to the characteristic of the peak type of the second white blood cell histogram, such that the accuracy of the counting and classification of white blood cells is improved.

Specifically, the method for classifying and counting white blood cells of the present application will be described in detail below with reference to the accompanying drawings. In the case of no conflict, the features in the embodiments and implementations described below can be combined with each other.

Figure 4:
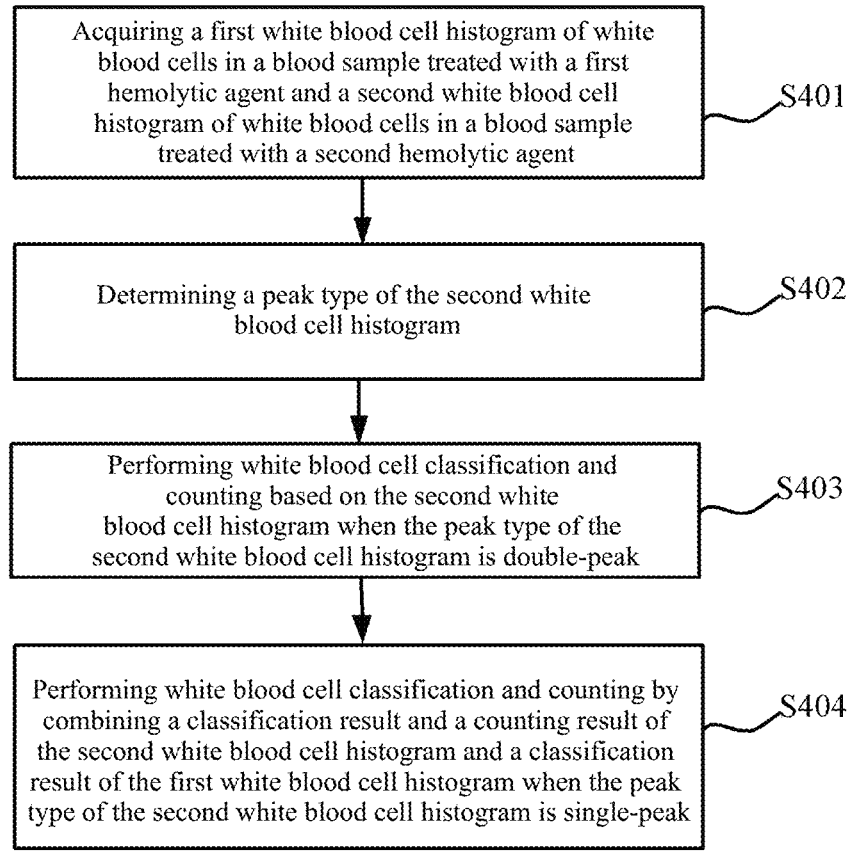
FIG. 4 is a flowchart of a method for classifying and counting white blood cells in one embodiment of the disclosure.

In an embodiment, as shown in FIG. 4, the method for classifying and counting white blood cells in this embodiment of the disclosure comprises steps S401 to S404 as follows.

First, in step S401, a first white blood cell histogram of white blood cells in a blood sample treated with a first hemolytic agent is acquired and a second white blood cell histogram of white blood cells in a blood sample treated with a second hemolytic agent is acquired, wherein a ghost value in the second white blood cell histogram is less than a ghost value in the first white blood cell histogram, and the ghost value in the second white blood cell histogram is less than a ghost value threshold.

The above-mentioned blood sample may be any animal or human blood sample, wherein the animal blood sample may be a blood sample of a dog, cat, etc., and the blood sample comprises white blood cells. In this embodiment, the animal blood sample is mainly taken as an example to explain and illustrate the method of the embodiments of the disclosure. However, it is conceivable that the method of the disclosure may also be applied to a human blood sample. Herein, the first white blood cell histogram and the second white blood cell histogram are both obtained by testing the blood sample on the basis of an electrical impedance method.

The blood sample may be treated with a diluent, a hemolytic agent, etc. The diluent is an isotonic solution having an acid-base buffer effect, and an appropriate ionic strength and conductivity. A diluting liquid is, for example, mainly composed of hypoxanthine or a xanthine compound or a salt thereof, or may be another diluent that can function as described above. The hemolytic agent is used to lyse red blood cells, so as to perform white blood cell classification and counting. The hemolytic agent comprises a surfactant, which may specifically comprise a cationic surfactant and a non-ionic surfactant. For example, the hemolytic agent may be mainly composed of a quaternary ammonium salt ionic surfactant, or may be any other surfactant that can function as described above.

Figure 2:
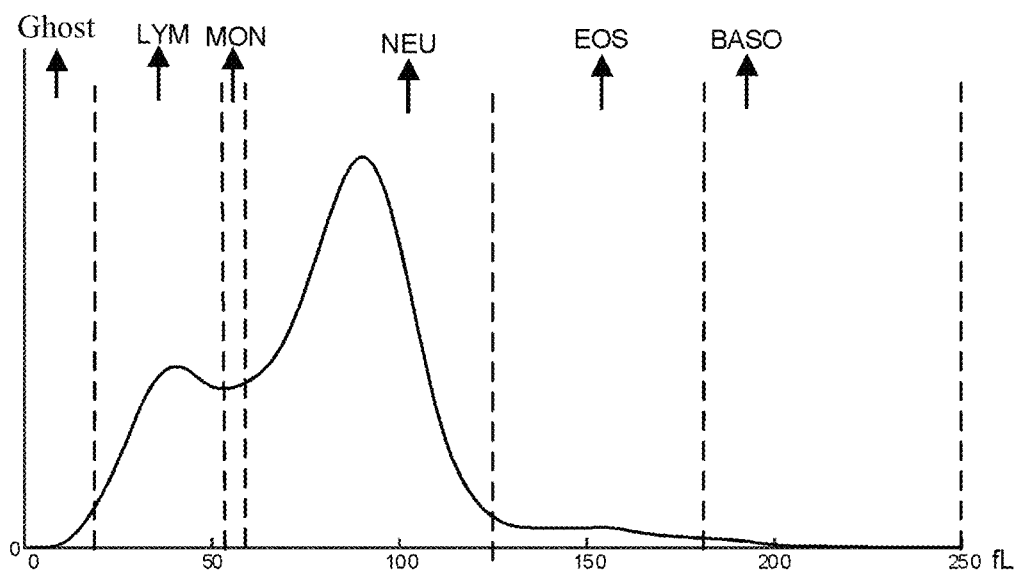
FIG. 2 is a schematic diagram of a second white blood cell histogram having two peaks in one embodiment of the disclosure.
Figure 3:
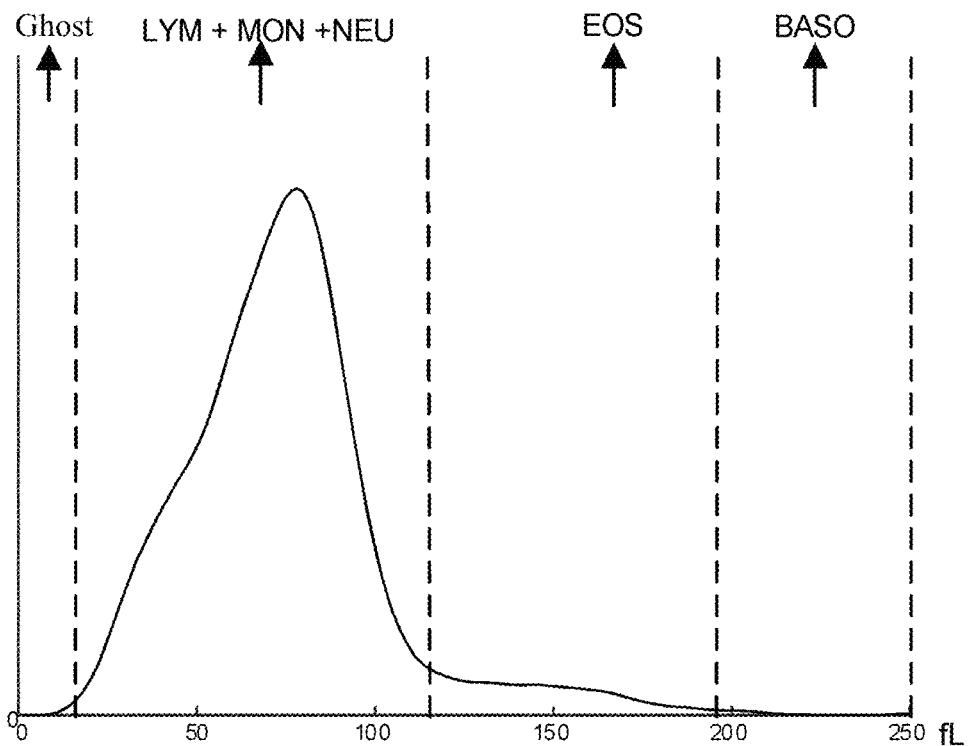
FIG. 3 is a schematic diagram of a second white blood cell histogram having one peak in one embodiment of the disclosure.

For a same blood sample, such as a human blood sample or an animal blood sample, especially an animal blood sample, two types of white blood cell histograms, for example, a first white blood cell histogram shown in FIG. 1 and a second white blood cell histogram shown in FIGS. 2 and 3, may be basically generated under different reaction conditions, such as different amounts of hemolytic agent, diluting liquid amounts, temperatures and agitation intensities.

In this embodiment, different reaction conditions are mainly obtained by changing at least one of a type, a dose, and a concentration of the hemolytic agent while keeping other reaction conditions (e.g. diluting liquid amounts, temperatures and agitation intensities) constant, such that different white blood cell histograms can be generated.

In an example, white blood cell testing is performed on the blood sample treated with the first hemolytic agent on the basis of the impedance method, so as to obtain the first white blood cell histogram, and white blood cell testing is performed on the blood sample treated with the second hemolytic agent on the basis of the impedance method, so as to obtain the second white blood cell histogram, wherein a ghost value in the second white blood cell histogram is less than a ghost value in the first white blood cell histogram, and the ghost value in the second white blood cell histogram is less than a ghost value threshold. The ghost value threshold may be properly set based on priori experiences. For example, when the ghost value in the second white blood cell histogram is less than the ghost value threshold, the impact on a counting result of white blood cells in the second white blood cell histogram can be ignored, and the accuracy of the counting result of white blood cells in the second white blood cell histogram is thus ensured. Optionally, a ghost region is demarcated in the second white blood cell histogram, the area of the ghost region or a counting result of ghosts included in the ghost region may be calculated as the ghost value, and then the ghost value is compared with the ghost value threshold to determine whether the acquired ghost value in the second white blood cell histogram is less than the ghost value threshold.

The first hemolytic agent and the second hemolytic agent may be different types of hemolytic agents, or may be a same hemolytic agent. In this embodiment, the case where the first hemolytic agent and the second hemolytic agent are a same hemolytic agent is mainly taken as an example to explain and illustrate the method of the disclosure, but this is not intended to limit the scope of the disclosure.

Optionally, a dose of the second hemolytic agent is greater than a dose of the first hemolytic agent, such that the number of ghosts in the blood sample treated with the first hemolytic agent is greater than the number of ghosts in the blood sample treated with the second hemolytic agent, which helps obtain the aforementioned second white blood cell histogram and first white blood cell histogram.

Figure 13:
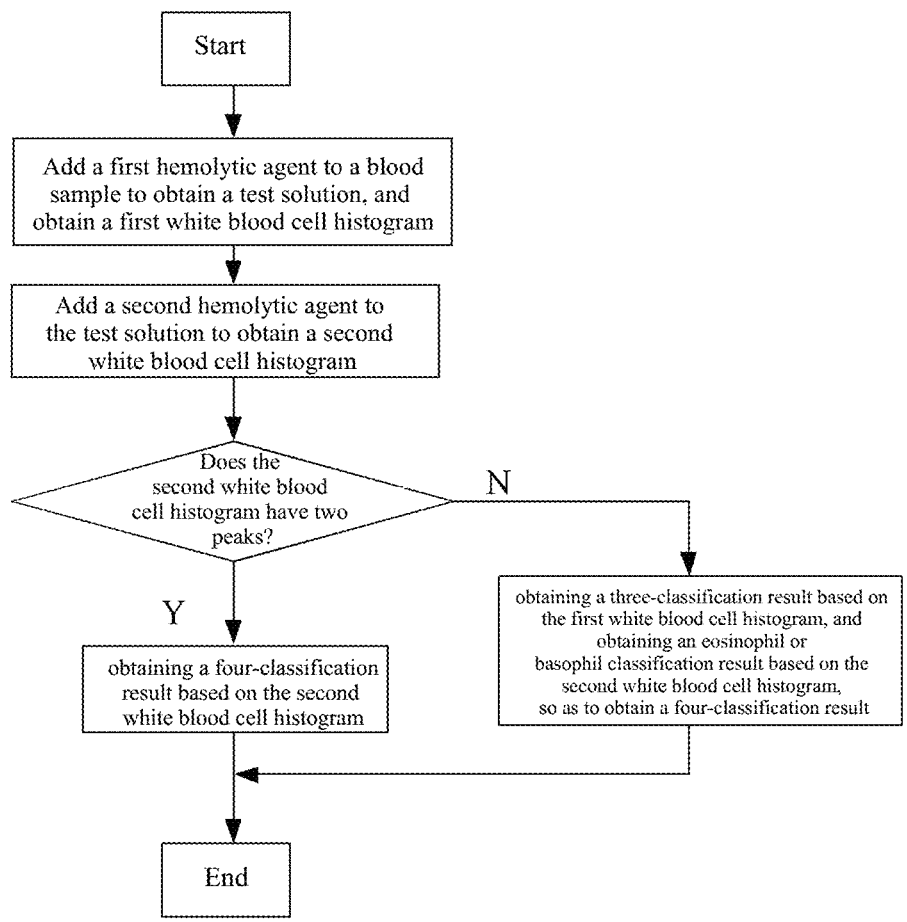
FIG. 13 is a flowchart of a method for implementing four-classification of white blood cells in one embodiment of the disclosure.
Figure 14:
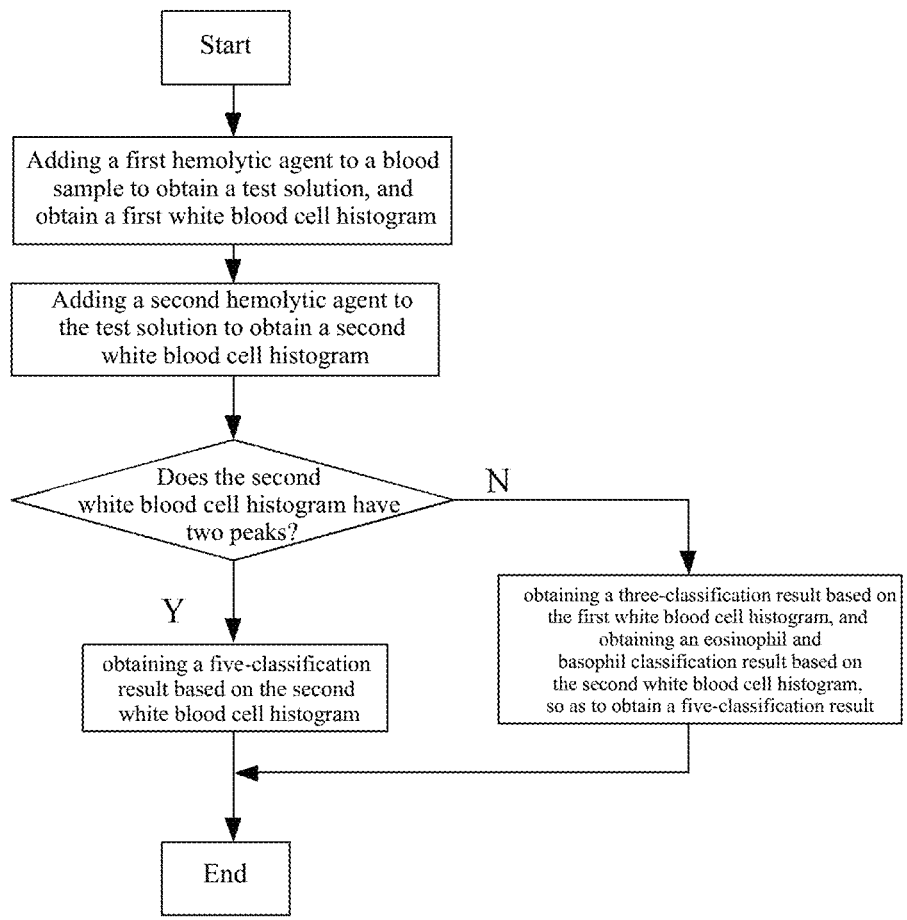
FIG. 14 is a flowchart of a method for implementing five-classification of white blood cells in one embodiment of the disclosure.

In an example, as shown in FIGS. 13 and 14, the method for obtaining the first white blood cell histogram and the second white blood cell histogram comprises: first adding the first hemolytic agent to the blood sample to obtain a test solution, and obtain the first white blood cell histogram; and then adding the second hemolytic agent to the test solution to obtain the second white blood cell histogram, wherein the first hemolytic agent and the second hemolytic agent may be a same hemolytic agent. For example, each time after treating the blood sample with the hemolytic agent, white blood cells in the blood sample are tested on the basis of the impedance method, so as to obtain the first white blood cell histogram and the second white blood cell histogram. Since the blood sample has contained the first hemolytic agent when the second hemolytic agent is added, the ghost value in the blood sample treated with the second hemolytic agent is less than that in the blood sample treated with the first hemolytic agent. Therefore, the second white blood cell histogram can be obtained by testing the blood sample treated with the second hemolytic agent on the basis of the impedance method.

Specifically, the addition dose of the first hemolytic agent and the addition dose of the second hemolytic agent may be properly set according to actual needs, or may be properly set based on priori experiences. For example, based on priori experiences through a number of experiments, such as 100 times of experiments, after different doses of the first hemolytic agent are added to a blood sample, a corresponding white blood cell histogram will be generated each time, and after analyzing characteristics of the white blood cell histogram generated each time, it is discovered that the white blood cell histogram generated within a threshold dose interval of the first hemolytic agent substantially meets requirements of the embodiments of the disclosure for the first white blood cell histogram (for example, in the embodiments of the disclosure, the first white blood cell histogram is required to meet the following requirements: a ghost value included in the first white blood cell histogram is greater than or equal to a ghost value threshold, and a peak type thereof is double-peak), such that a range of addition dose of the first hemolytic agent can be substantially determined, and the addition dose of the first hemolytic agent is thus determined.

Similarly, based on priori experiences through a number of experiments, such as 100 times of experiments, the second hemolytic agent is added to the blood sample treated with a predetermined dose (the predetermined dose being within the foregoing threshold dose interval of the first hemolytic agent) of first hemolytic agent, a corresponding white blood cell histogram will be generated each time, and after analyzing characteristics of the white blood cell histogram generated each time, it is discovered that the white blood cell histogram generated within a threshold dose interval of the second hemolytic agent substantially meets requirements of the embodiments of the disclosure for the second white blood cell histogram (for example, in the embodiments of the disclosure, the second white blood cell histogram is required to meet the following requirements: a ghost value in the second white blood cell histogram is less than a ghost value in the first white blood cell histogram, and the ghost value in the second white blood cell histogram is less than a ghost value threshold), such that a range of addition dose of the second hemolytic agent can be substantially determined, and the addition dose of the second hemolytic agent is thus determined.

In another example, the acquiring a first white blood cell histogram of white blood cells in a blood sample treated with a first hemolytic agent and a second white blood cell histogram of white blood cells in a blood sample treated with a second hemolytic agent comprises: sequentially adding a hemolytic agent to the same blood sample at least three times, wherein the hemolytic agent added each time comprises at least one of the first hemolytic agent and the second hemolytic agent, and a corresponding white blood cell histogram is generated after each addition of the first hemolytic agent and/or the second hemolytic agent; and selecting two successively generated white blood cell histograms as the first white blood cell histogram and the second white blood cell histogram, respectively, for example, selecting two successive white blood cell histograms, which satisfy the following requirements, as the first white blood cell histogram and the second white blood cell histogram, respectively, wherein a ghost value included in the first white blood cell histogram is greater than or equal to a ghost value threshold, and a peak type of the first white blood cell histogram is double-peak; and a ghost value in the second white blood cell histogram is less than the ghost value in the first white blood cell histogram, and the ghost value in the second white blood cell histogram is less than the ghost value threshold.

It should be noted that the same blood sample may be sampled into a same reaction cell or counting cell, and then the first hemolytic agent and the second hemolytic agent are added for the foregoing reaction. Alternatively, the same blood sample may be sampled into at least two reaction cells or counting cells, and then the first hemolytic agent and the second hemolytic agent are added for the foregoing reaction. In either way, the foregoing first white blood cell histogram and second white blood cell histogram can be finally obtained.

It should be noted that different animal blood samples of different animal types (e.g. dog, cat, pig, sheep, cattle, etc.) may have different characteristics of internal blood cells, which may make it possible that animal blood samples of different animal types may require the addition of different doses of the first hemolytic agent and the second hemolytic agent. Therefore, the dose of the first hemolytic agent and the dose of the second hemolytic agent may also be properly selected according to the animal types to which the animal blood samples belong.

In an example, when the method is applied to an animal-type hematology analyzer, the hematology analyzer is still provided with a test mode selection module, for example, a test mode key provided on the hematology analyzer, and before testing the blood sample of the embodiment of the disclosure, the method further comprises: selecting a predetermined test mode to test the blood sample according to an animal type to which the blood sample belongs, so as to obtain the first white blood cell histogram and the second white blood cell histogram, wherein the predetermined test mode may comprise a test mode for a blood sample of a cat, a dog, or another type of animal.

In an example, by taking a blood sample of a cat as an example, after the sequential addition of the same hemolytic agent to the same blood sample at least two times, the obtained white blood cell histograms may comprise a white blood cell histogram having ghosts (with a ghost value being greater than or equal to a ghost value threshold) and having a single peak, and may also comprise a white blood cell histogram having ghosts (with a ghost value being greater than or equal to a ghost value threshold) and having two peaks. In this embodiment, in order to facilitate the classification of the first white blood cell histogram, the white blood cell histogram having ghosts (with a ghost value being greater than or equal to a ghost value threshold) and having two peaks is selected as the first white blood cell histogram.

Therefore, still as shown in FIG. 4, the method in this embodiment of the disclosure further comprises step S402 of determining a peak type of the second white blood cell histogram.

The peak type of the second white blood cell histogram may be determined using any suitable method. The peak type refers to, for example, the number of peaks included in the second white blood cell histogram. For example, if there is one peak, the peak type thereof is single-peak, and if there are two peaks, the peak type thereof is double-peak, and so on.

Figure 5:
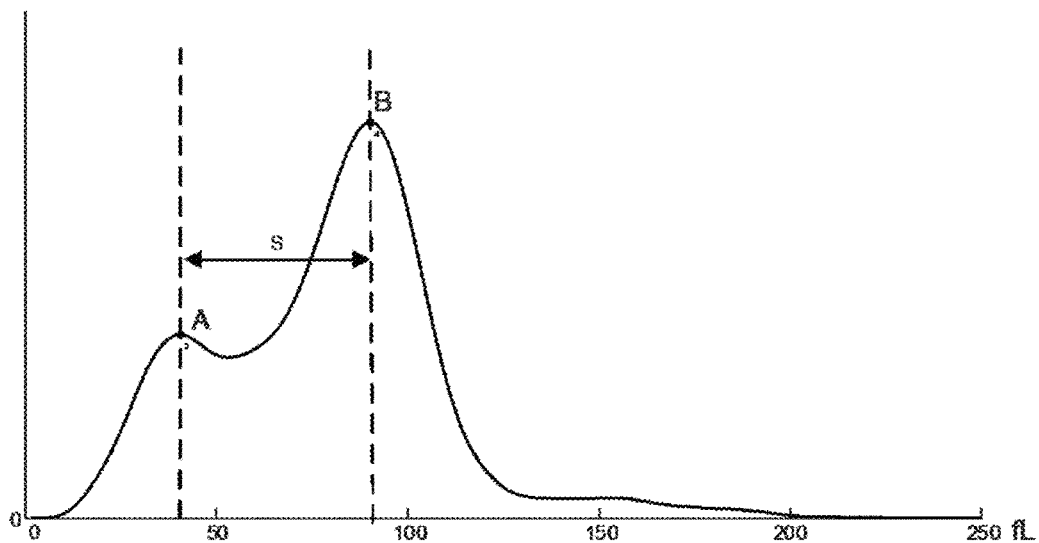
FIG. 5 is a schematic diagram of a second white blood cell histogram having two peaks in one embodiment of the disclosure.

In a specific example, the method for determining the peak type of the second white blood cell histogram comprises: determining the peak type of the second white blood cell histogram according to the number of peak points in the second white blood cell histogram, wherein if there are two peak points, and a distance between the two peak points is greater than a preset distance, the second white blood cell histogram is double-peak; otherwise, the second white blood cell histogram is single-peak. The preset distance may be properly set according to characteristics of the actual white blood cell histogram. Herein, the preset distance may refer to a volume between adjacent peak points. For example, the preset distance may be about 40 fL or other suitable distances. In the second white blood cell histogram shown in FIG. 5, it is determined that there are two peak points A and B, and a distance between the peak points A and B is approximately 50 fL, which is greater than the preset distance S. Therefore, it can be determined that the peak type of the second white blood cell histogram shown in FIG. 5 is double-peak.

It should be noted that herein, during the determination of peak points of a white blood cell histogram (e.g. the first white blood cell histogram and the second white blood cell histogram), at both the left and right sides of a peak point, there may be at least a predetermined number of consecutive points with ordinate values less than an ordinate value of the peak point. The predetermined number is properly set according to actual needs, for example, at least 10, 20, 30, 40, or other suitable number of points, etc. Exemplarily, all points on a curve of the white blood cell histogram may be traversed from a minimum volume ($V_{min}$) or a maximum volume ($V_{max}$) of the white blood cell histogram. For example, all the points on the curve of the white blood cell histogram are traversed from the minimum volume and in a volume increasing direction, when the ordinate values of the points gradually increase to a maximum value, and as the volume continues to increase, ordinate values of the at least a predetermined number of consecutive points start to decrease from the maximum value, and it can be determined that the maximum value is the peak point. Similarly, all the points on the curve of the white blood cell histogram can also be traversed from the minimum volume and in a volume decreasing direction, when the ordinate values of the points gradually increase to a maximum value, and as the volume continues to decrease, ordinate values of the at least a predetermined number of consecutive points start to decrease from the maximum value, and it can be determined that the maximum value is the peak point.

Still referring to FIG. 4, in step S403, white blood cell classification and counting are performed on the basis of the second white blood cell histogram when the peak type of the second white blood cell histogram is double-peak.

In a specific example, as shown in FIG. 13, when the peak type of the second white blood cell histogram is double-peak, four-classification is performed on the second white blood cell histogram determined as double-peak, and a classification result of the four-classification is used as a final four-classification result of white blood cells in the blood sample.

It should be noted that three-classification, four-classification, or five-classification, etc. is performed on the white blood cell histogram herein. The three-classification may refer to the classification of white blood cells into a first type of white blood cells, a second type of white blood cells, and a third type of white blood cells. The four-classification may refer to the classification of white blood cells into a first type of white blood cells, a second type of white blood cells, a third type of white blood cells, and a fourth type of white blood cells. The five-classification may refer to the classification of white blood cells into a first type of white blood cells, a second type of white blood cells, a third type of white blood cells, a fourth type of white blood cells, and a fifth type of white blood cells. For different types of blood samples, white blood cells therein may contain different types of white blood cells. For example, animal white blood cells may contain the first to fifth type of white blood cells in sequence from a minimum volume, wherein the first type of white blood cells may be lymphocytes, the second type of white blood cells may be monocytes, the third type of white blood cells may be neutrophil granulocytes, the fourth type of white blood cells may be eosinophil granulocytes, and the fifth type of white blood cells may be basophil granulocytes.

The four-classification may be performed on the second white blood cell histogram by using any suitable method. For example, as shown in FIG. 6, the method for performing the four-classification on the second white blood cell histogram may comprise steps A1 to A4 as follows.

Figure 6:
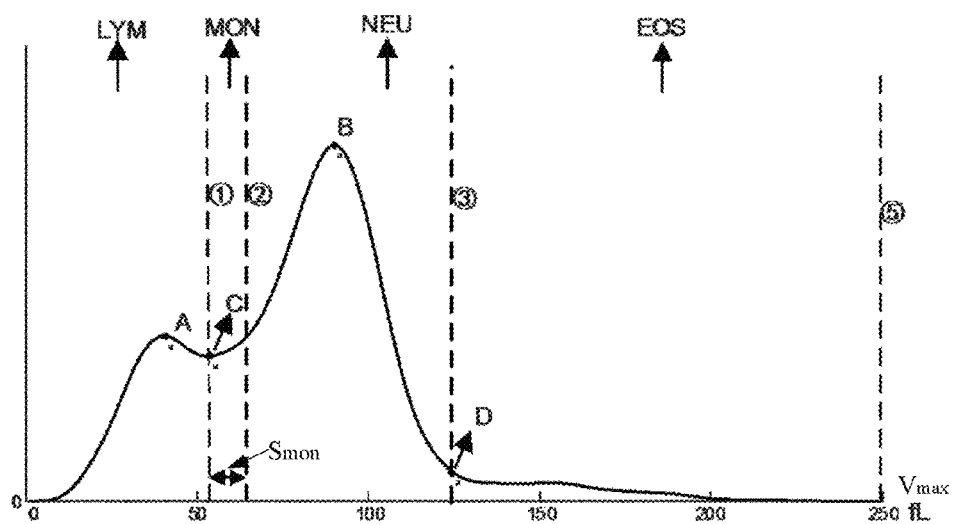
FIG. 6 is a schematic diagram of four-classification of a second white blood cell histogram having two peaks in one embodiment of the disclosure.

First, in step A1, a first demarcation line 1 between a first type of white blood cells and a second type of white blood cells is determined according to a trough point C between two peak points A and B in the second white blood cell histogram, wherein a volume of the first type of white blood cells is less than a volume of the second type of white blood cells; and a region in the second white blood cell histogram that has a volume less than a volume corresponding to the first demarcation line represents the first type of white blood cells (e.g. lymphocytes (LYM) shown in FIG. 6).

The two peak points A and B in the second white blood cell histogram may be determined by using the method mentioned above, and the trough point C may be determined by using any suitable method. For example, the trough point C is a minimum point between the peak points A and B that corresponds to a minimum ordinate value.

Next, in step A2, still as shown in FIG. 6, a second demarcation line 2 between the second type of white blood cells (e.g. monocytes (MON)) and a third type of white blood cells (e.g. neutrophil granulocytes (NEU)) is determined according to the first demarcation line 1, wherein the second demarcation line is separated from the first demarcation line by a first predetermined volume, and a volume corresponding to the second demarcation line is greater than a volume corresponding to the first demarcation line.

The first predetermined volume Smon may be properly set based on priori experiences. For example, under specific reaction conditions, reaction temperatures, and doses of reagents (including a hemolytic agent and a diluent), a volume between the trough point and the actual second demarcation line under these specific conditions, particularly under a specific dose of the hemolytic agent used, is obtained after multiple tests, so as to determine the first predetermined volume Smon, for example, Smon is about 20 fL, wherein under different reaction conditions, reaction temperatures, and doses of reagents (including a hemolytic agent and a diluent), a location of the trough point and a value of the first predetermined volume Smon will also be different, which may be properly adjusted according to actual situations.

Next, in step A3, a second demarcation point D on a curve of the second white blood cell histogram at which a slope is greater than a second threshold slope K for the first time is searched for from a maximum volume Vmax (e.g. Vmax=250 fL) of the second white blood cell histogram and in a volume decreasing direction.

The maximum volume Vmax may refer to an end position of white blood cells in the white blood cell histogram. Generally, the curve of the initial white blood cell histogram shows an upward trend on the right side of the first peak point A. Points on a predetermined segment of the curve of the second white blood cell histogram from the maximum volume Vmax and in a volume decreasing direction have a slope is less than or equal to 0. Therefore, the value of the second threshold slope K is set to be less than zero. Specifically, the value of the second threshold slope K may be set according to actual situations.

Next, in step A4, a third demarcation line between the third type of white blood cells and a fourth type of white blood cells is determined on the basis of the second demarcation point, and the third demarcation line is a straight line which passes through the second demarcation point D and is perpendicular to the horizonal axis of the second white blood cell histogram, thereby achieving the four-classification of white blood cells, wherein a region between the second demarcation line and third demarcation line represents the third type of white blood cells, such as neutrophil granulocytes (NEU), and a region between the third demarcation line and Vmax is the fourth type of white blood cells (e.g. eosinophil granulocytes (EOS)).

In another specific example, as shown in FIG. 14, when the peak type of the second white blood cell histogram is double-peak, five-classification is performed on the second white blood cell histogram determined as double-peak, and a classification result of the five-classification is used as a final five-classification result of white blood cells in the blood sample.

Figure 7:
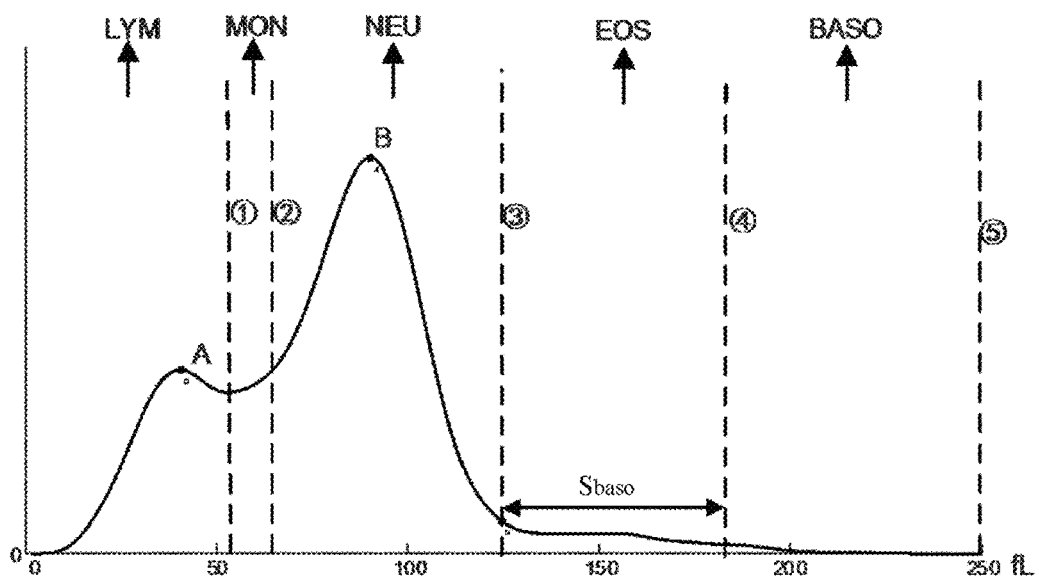
FIG. 7 is a schematic diagram of five-classification of a second white blood cell histogram having two peaks in one embodiment of the disclosure.

The five-classification may be performed on the second white blood cell histogram by using any suitable method. For example, as shown in FIG. 7, the method for performing the five-classification on the second white blood cell histogram may comprise steps A1 to A4 of the foregoing four-classification, and further comprises: determining a fourth demarcation line between the fourth type of white blood cells and a fifth type of white blood cells according to the third demarcation line, wherein the fourth demarcation line is separated from the third demarcation line by a second predetermined volume $S_{baso}$, a volume corresponding to the fourth demarcation line is greater than a volume corresponding to the third demarcation line, and therefore a region in the second white blood cell histogram, that is located between the third demarcation line and the fourth demarcation line, represents the fourth type of white blood cells; and a region in the second white blood cell histogram that has a volume greater than the volume corresponding to the fourth demarcation line, that is, the region between the fourth demarcation line and the maximum volume represents the fifth type of white blood cells (e.g. basophil granulocytes (BASO)).

The second predetermined volume $S_{baso}$ may be properly set based on priori experiences. For example, the second predetermined volume $S_{baso}$ is about 55 fL, or other suitable volumes, wherein a value of the predetermined volume may also vary due to different reaction conditions. Therefore, the above-mentioned value is merely an example, and is not intended to limit the scope of the disclosure.

It should be noted that herein, in a rectangular coordinate system of the white blood cell histogram, cell volume is taken as the abscissa, and the number of cell particles of different volumes is taken as the ordinate, wherein the first demarcation line, the second demarcation line, the third demarcation line, and the fourth demarcation line are all perpendicular to the horizontal axis (that is, the axis of abscissas) of the rectangular coordinate system of the white blood cell histogram.

Further, performing white blood cell classification and counting on the basis of the second white blood cell histogram further comprises: obtaining a classification result of each type of white blood cells according to a proportion of each of the first type of white blood cells, the second type of white blood cells, the third type of white blood cells, the fourth type of white blood cells, and the fifth type of white blood cells in the second white blood cell histogram after classification, for example, obtaining the classification result of the first type of white blood cells LYM2%, the classification result of the second type of white blood cells MON2%, the classification result of the third type of white blood cells NEU2%, the classification result of the fourth type of white blood cells EOS2%, and the classification result of the fifth type of white blood cells BASO2%, wherein results are shown in Table 1 below for the four-classification, and results are shown in Table 2 below for the five-classification; and calculating a counting result of each type of white blood cells according to the classification result of each type of white blood cells and the counting result of white blood cells. For example, as shown in Table 1, the counting result of white blood cells in the second white blood cell histogram is WBC2. The counting result of white blood cells is also the total particle number of white blood cells tested in the blood sample, and the counting result of white blood cells may be directly obtained according to the number of pulse signals obtained when the blood sample is tested on the basis of the impedance method. The counting result of white blood cells may also be calculated according to the generated second white blood cell histogram. For example, the counting result of white blood cells may be obtained by adding the particle number corresponding to the ordinate at each integral volume in the second white blood cell histogram and rounding the addition result, or by using other counting methods.

Calculating a counting result of each type of white blood cells according to the classification result of each type of white blood cells and the counting result of white blood cells may comprise: multiplying the classification result of each type of white blood cells by the counting result of white blood cells to calculate a counting result of each type of white blood cells, which is shown in Tables 1 and 2 below.

The list of five-classification results and counting results is shown in FIG. 2:

TABLE 1

List of four-classification results and counting results

| | Counting and classification parameter results | | | |
|---|---|---|---|---|
| | Second hemolytic agent | First hemolytic agent | Final white blood cell classification and counting results | Implementation of classification |
| Double-peak | WBC2, LYM2%, MON2%, NEU2%, EOS2% | — | WBC = WBC2 LYM % = LYM2%, MON % = MON2%, NEU % = NEU2%, EOS % = EOS2%, LYM# = LYM2%* WBC2, MON# = MON2%* WBC2, NEU# = NEU2%* WBC2, EOS# = EOS2%* WBC2 | Four-classification |
| Single-peak | WBC2, EOS2%, | LYM1%, MON1%, NEU1%, | WBC = WBC2 LYM % = LYM1%, MON % = MON1%, NEU % = NEU1%-EOS2%, EOS % = EOS2%, LYM# = LYM1%* WBC2, MON# = MON1%* WBC2, NEU# = (NEU1%-EOS2%)* WBC2, EOS# = EOS2%* WBC2 | |

TABLE 2

List of five-classification results and counting results

| | Counting and classification parameter results | | Final white blood cell classification and counting results | Implementation of classification |
|---|---|---|---|---|
| | Second hemolytic agent | First hemolytic agent | | |
| Double-peak | WBC2, LYM2%, MON2%, NEU2%, EOS2%, BASO2% | — | WBC = WBC2, LYM % = LYM2%, MON % = MON2%, NEU % = NEU2%, EOS % = EOS2%, BASO % = BASO2% LYM# = LYM2%* WBC2, MON# = MON2%* WBC2, NEU# = NEU2%* WBC2, EOS# = EOS2%* WBC2, BASO# = BASO2%* WBC2 | Five-classification |
| Single-peak | WBC2, EOS2%, BASO2% | LYM1%, MON1%, NEU1%, | WBC = WBC2 LYM % = LYM1%, MON % = MON1%, NEU % = NEU1%-EOS2%-BASO2%, EOS % = EOS2%, BASO % = BASO2% LYM# = LYM1%*WBC2, MON# = MON1%*WBC2, NEU# = (NEU1%-EOS2%-BASO2%)* WBC2, EOS# = EOS2%*WBC2, BASO# = BASO2%* WBC2 | |

Finally, as shown in FIGS. 13 and 14 and Tables 1 and 2, the four-classification result and counting result, and the five-classification result and counting result of the second white blood cell histogram are directly used as a final four-classification result and counting result, and five-classification result and counting result of white blood cells in the blood sample. Because the ghost value in the second white blood cell histogram determined as double-peak is less than the ghost value threshold, the second white blood cell histogram is hardly interfered by ghosts. Therefore, the counting result of the second white blood cell histogram can accurately reflect the counting result of white blood cells in the blood sample. Moreover, since the peak type of the second white blood cell histogram is double-peak, and various particle populations in white blood cells are distributed away from each other, so that a four-classification or five-classification of white blood cells is facilitated to obtain an accurate classification result. Therefore, the use of the classification result and counting result of the second white blood cell histogram determined as double-peak as the final classification result and counting result of white blood cells provides a higher accuracy.

Further, as shown in FIG. 4, in step S404, white blood cell classification and counting are performed by combining a classification result and a counting result of the second white blood cell histogram and a classification result of the first white blood cell histogram when the peak type of the second white blood cell histogram is single-peak.

In an example, the performing white blood cell classification and counting by combining a classification result and a counting result of the second white blood cell histogram and a classification result of the first white blood cell histogram comprises the following steps:

first, performing classification and counting on the second white blood cell histogram determined as single-peak, to obtain a counting result of white blood cells and a classification result of eosinophil granulocytes and/or a classification result of basophil granulocytes in the white blood cells.

Figure 8:
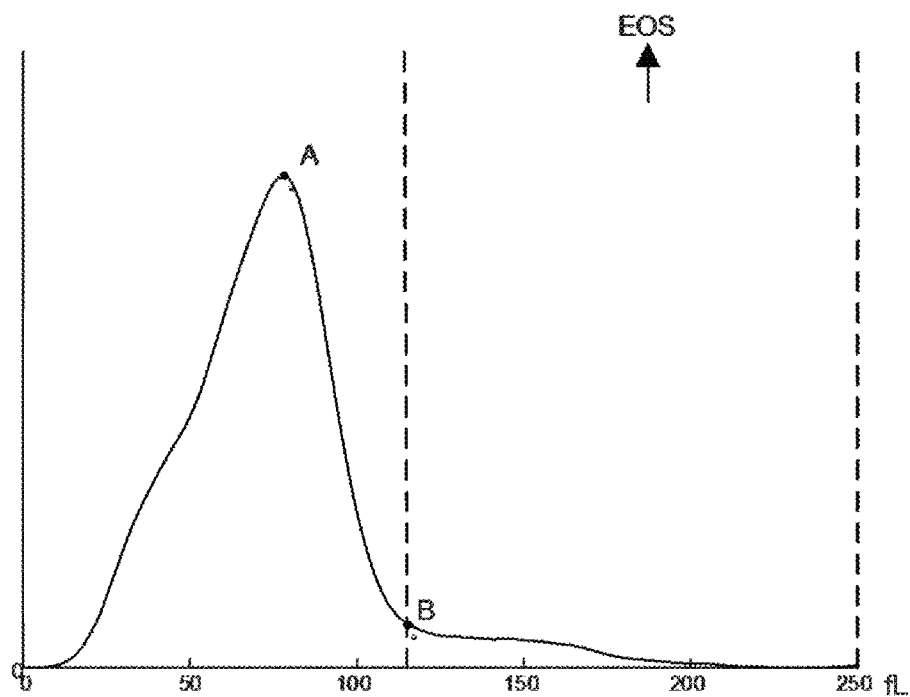
FIG. 8 is a schematic diagram of classification of a second white blood cell histogram having one peak in one embodiment of the disclosure.

In an example, eosinophil granulocytes (EOS) may be classified only from the second white blood cell histogram determined as single-peak, and the eosinophil granulocytes (EOS) may be classified therefrom by using any suitable method. For example, as shown in FIG. 8, the method for performing classification the second white blood cell histogram determined as single-peak comprises: determining a peak point A of the second white blood cell histogram, wherein since the second white blood cell histogram is single-peak, the peak point A is a maximum point on the second white blood cell histogram, that is, a point with the largest ordinate value; and then searching, from the peak point A and in a volume increasing direction, for a first demarcation point B on a curve of the second white blood cell histogram at which a slope is greater than a first threshold slope $K_{eos}$ for the first time, wherein a region in the second white blood cell histogram that has a volume greater than a volume of the first demarcation point B represents the eosinophil granulocytes.

A value of the first threshold slope $K_{eos}$ may be properly set according to actual needs. For example, the first threshold slope $K_{eos}$ is less than 0.

In another example, alternatively, basophil granulocytes (BASO) may be classified only from the second white blood cell histogram determined as single-peak. For example, the basophil granulocytes (BASO) may be classified from the second white blood cell histogram by using the following method, which comprises determining a fourth demarcation line from the maximum volume Vmax (e.g. 250 fL) and in a volume decreasing direction, wherein the fourth demarcation line is separated from the maximum volume by a predetermined volume (e.g. about 50 fL); the predetermined volume may be properly set based on priori experiences, and is not particularly limited; and a region in the second white blood cell histogram that has a volume greater than a volume corresponding to the fourth demarcation line represents the basophil granulocytes.

Figure 9:
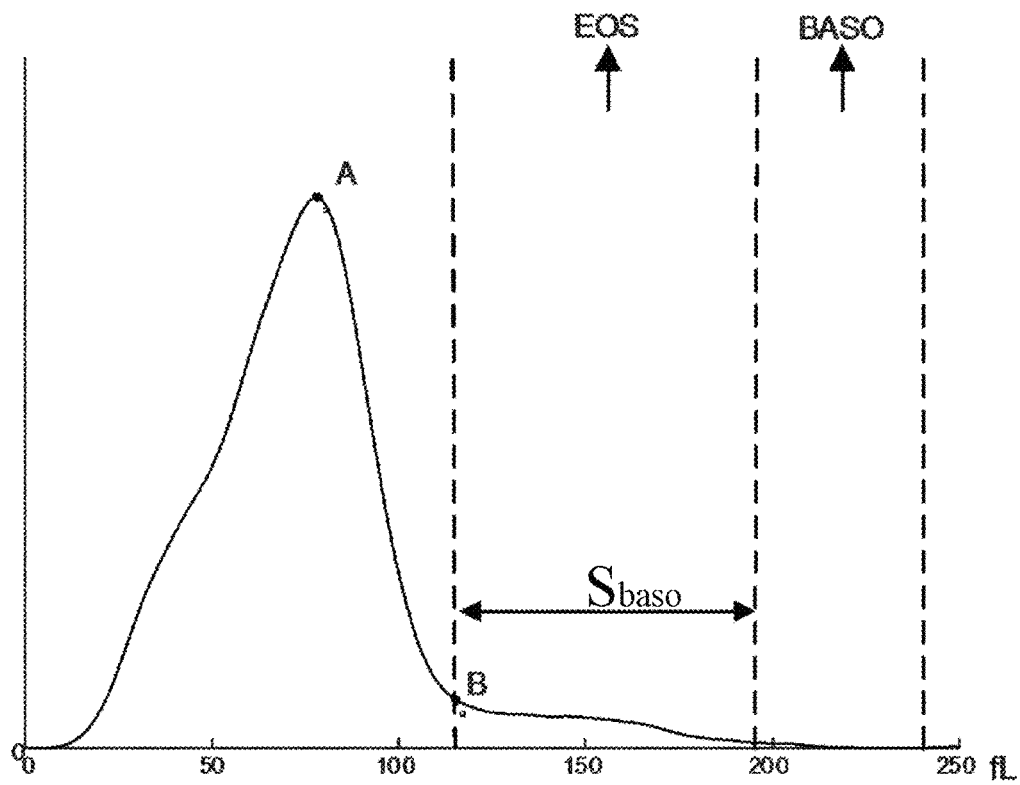
FIG. 9 is a schematic diagram of classification of a second white blood cell histogram having one peak in another embodiment of the disclosure.

In other examples, as shown in FIG. 9, alternatively, eosinophil granulocytes and basophil granulocytes may be classified from the second white blood cell histogram determined as single-peak. For example, a first demarcation point B may be first determined by using the method shown in FIG. 8, and then a fourth demarcation line between the eosinophil granulocytes and the basophil granulocytes may be determined according to a third demarcation line passing through the first demarcation point B, wherein the fourth demarcation line is separated from the third demarcation line by a predetermined volume $S_{baso}$, the predetermined volume $S_{baso}$ may be properly set based on priori experiences, for example, the predetermined volume $S_{baso}$ is about 75 fL, and a volume corresponding to the fourth demarcation line is greater than a volume corresponding to the third demarcation line; a region between the third demarcation line and the fourth demarcation line represents the eosinophil granulocytes (EOS); and a region in the second white blood cell histogram that has a volume greater than the volume of the fourth demarcation line, e.g. the region between the fourth demarcation line and the maximum volume, represents the basophil granulocytes (BASO).

The above-mentioned method for classifying eosinophil granulocytes and/or basophil granulocytes from the second histogram determined as single-peak is merely used as an example, and other suitable methods may also apply equally to the present application.

Optionally, the classification result of eosinophil granulocytes is a proportion of a region of the eosinophil granulocytes in the second white blood cell histogram, for example, ESO2% shown in Tables 1 and 2; and the classification result of basophil granulocytes is a proportion of a region of the eosinophil granulocytes in the second white blood cell histogram, for example, BASO2% shown in Table 2.

An at least three-classification may be performed on the first white blood cell histogram after the step of determining a peak type of the second white blood cell histogram or before the step of determining the peak type. In this embodiment, the case of performing a three-classification on the first white blood cell histogram is mainly taken as an example. For example, after the step of determining a peak type of the second white blood cell histogram, if it is determined that the second white blood cell histogram is single-peak, and the peak type of the first white blood cell histogram is double-peak, the at least three-classification is performed on the first white blood cell histogram.

In an example, when it is determined that the second white blood cell histogram is single-peak, the method for performing the three-classification on the first white blood cell histogram comprises: demarcating a ghost region in the first white blood cell histogram; removing the ghost region from the first white blood cell histogram; and performing the three-classification on the first white blood cell histogram with the ghost region removed.

The ghost region may be demarcated in the first white blood cell histogram by using any suitable method. For example, a demarcation line between ghosts and white blood cells is searched for; and the ghost region is demarcated according to the demarcation line, wherein a region in the first white blood cell histogram that has a volume less than a volume corresponding to the demarcation line is the ghost region.

Figure 10:
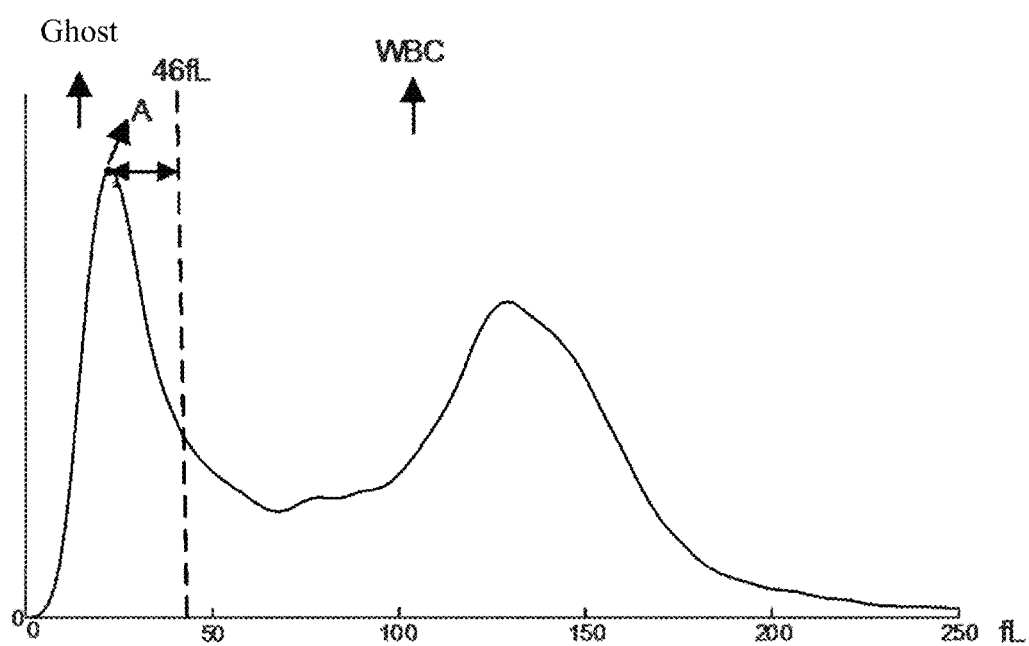
FIG. 10 is a schematic diagram of demarcating a ghost region in a first white blood cell histogram in one embodiment of the disclosure.

The demarcation line between the ghosts and the white blood cells may be determined by using any suitable method. In an example, as shown in FIG. 10, the searching for the demarcation line between the ghosts and the white blood cells comprises: determining a first peak point A in the first white blood cell histogram from the minimum volume and in a volume increasing direction; and determining the demarcation line according to the first peak point A, wherein the demarcation line is separated from the first peak point by a predetermined volume, and a volume corresponding to the demarcation line is greater than a volume corresponding to the first peak point. For example, the predetermined volume may be about 46 fL.

Figure 11:
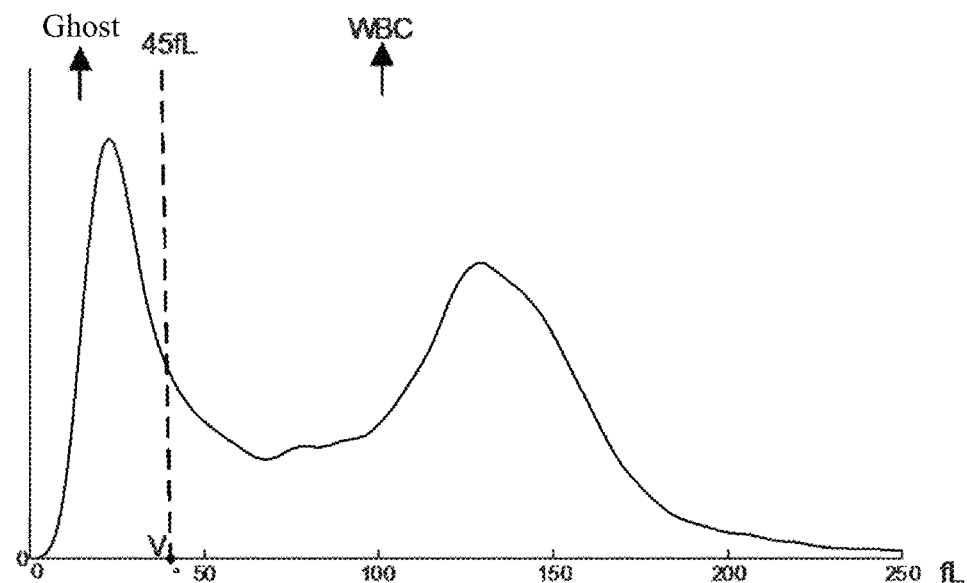
FIG. 11 is a schematic diagram of demarcating a ghost region in a first white blood cell histogram in another embodiment of the disclosure.

The method for determining the ghost region may also be as shown in FIG. 11. A fixed volume V is set, and the fixed volume V may be properly set according to actual situations, for example, V being equal to about 45 fL. Thus, a region in the first white blood cell histogram that has a volume less than the fixed volume V is the ghost region.

Figure 12:
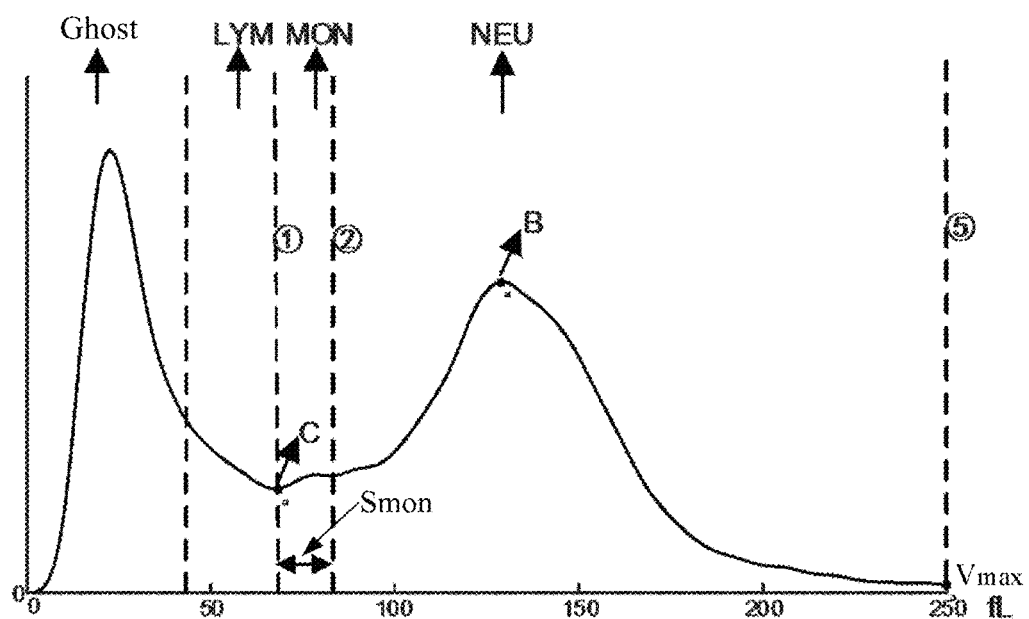
FIG. 12 is a schematic diagram of three-classification of a first white blood cell histogram in one embodiment of the disclosure.

Further, the three-classification may be performed on the first white blood cell histogram with the ghost region removed by using any suitable method. For example, as shown in FIG. 12, performing the three-classification on the first white blood cell histogram with the ghost region removed comprises: obtaining a first trough point C in the first white blood cell histogram from the demarcation line between the ghost region and the white blood cells and in a volume increasing direction, wherein the first trough point C may be determined by using any suitable method, for example, ordinate values of a predetermined number of points continuously increase from the first trough point C and in a volume decreasing direction, and ordinate values of a predetermined number of points continuously decrease from the first trough point C and in a volume increasing direction; demarcating a first demarcation line between a first type of white blood cells and a second type of white blood cells on the basis of the first trough point, wherein a volume of the first type of white blood cells is less than a volume of the first trough point, and a volume of the second type of white blood cells is greater than the volume corresponding to the first trough point; and determining a second demarcation line between the second type of white blood cells and a third type of white blood cells according to the first demarcation line, wherein the first demarcation line is separated from the second demarcation line by a predetermined volume $S_{mon}$, for example, Smon being 28 fL or other suitable values; a region between the demarcation line between white blood cells and the ghost region and the first demarcation line represents the first type of white blood cell; a region between the first demarcation line and the second demarcation line represents the second type of white blood cells; and a region having a volume greater than a volume corresponding to the second demarcation line represents the third type of white blood cells, that is, a region between the second demarcation line and the maximum volume Vmax represents the third type of white blood cells. The classification result of each type of white blood cells in the first white blood cell histogram is a proportion of the type of white blood cells in the first white blood cell histogram with the ghost region removed. Optionally, the first type of white blood cells are lymphocytes, the second type of white blood cells are monocytes, and the third type of white blood cells are neutrophil granulocytes.

Optionally, the classification result of each of the first type of white blood cells, the second type of white blood cells, and the third type of white blood cells is a proportion of the type of white blood cells in the first white blood cell histogram with the ghost region removed. For example, as shown in Tables 1 and 2, the first type of white blood cells are lymphocytes, and the classification result thereof is LYM1%; the second type of white blood cells are monocytes MON, and the classification result thereof is MON1%; and the third type of white blood cells is neutrophil granulocytes, and the classification result thereof is NEU1%.

Since particle populations of the second white blood cell histogram determined as single-peak are distributed close to each other and can hardly be further classified, a final at least four-classification white blood cell classification result of white blood cells in a blood sample is obtained according to the classification result of the second white blood cell histogram and the classification result of the first white blood cell histogram after the at least three-classification, the first white blood cell histogram comprising a first type of white blood cells, a second type of white blood cells, and a third type of white blood cells. For example, as shown in Tables 1 and 2, the classification result of eosinophil granulocytes and/or the classification result of basophil granulocytes in the second white blood cell histogram is used as a final classification result of eosinophil granulocytes and/or a final classification result of basophil granulocytes in white blood cells in the blood sample. The classification result (ESO2%) of eosinophil granulocytes and/or classification result (BASO2%) of basophil granulocytes in the second white blood cell histogram are/is subtracted from the classification result (e.g. NEU1%) of the third type of white blood cells in the first white blood cell histogram after the at least three-classification to obtain a final classification result (NEU %) of the third type of white blood cells in white blood cells in the blood sample.

In the example shown in FIG. 13, when it is determined that the second white blood cell histogram is not double-peak, that is, the second white blood cell histogram is single-peak, after eosinophil granulocytes or basophil granulocytes are classified from the second white blood cell histogram determined as single-peak, the classification result of the eosinophil granulocytes or the classification result of the basophil granulocytes is combined with the three-classification result of the first white blood cell histogram after the three-classification, so as to obtain a final four-classification result of white blood cells in the blood sample, which is shown in Table 1.

In the example shown in FIG. 14, when it is determined that the second white blood cell histogram is not double-peak, that is, the second white blood cell histogram is single-peak, after eosinophil granulocytes and basophil granulocytes are classified from the second white blood cell histogram determined as single-peak, the classification results of the eosinophil granulocytes and the basophil granulocytes are combined with the three-classification result of the first white blood cell histogram after the three-classification, so as to obtain a final five-classification result of white blood cells in the blood sample, which is shown in Table 2.

Since the interference from ghosts in the second white blood cell histogram determined as single-peak is almost negligible, the white blood cell count result WBC2 in the second white blood cell histogram may be used as a final counting result of white blood cells in the blood sample, that is, a result of the total number of white blood cells.

Further, a counting result of each type of white blood cells in the blood sample may also be calculated on the basis of the at least four-classification result of white blood cells and the counting result of white blood cells. For example, a final four-classification result of white blood cells in the blood sample is shown in Table 1. A final counting result LYM# of the first type of white blood cells, lymphocytes, is a product of the classification result LYM1% of lymphocytes in the first white blood cell histogram and the counting result WBC2 of white blood cells in the second white blood cell histogram; a final counting result MON# of the second type of white blood cells, monocytes, is a product of the classification result MON1% of monocytes in the first white blood cell histogram and the counting result WBC2 of white blood cells in the second white blood cell histogram; and finally, a counting result of eosinophil granulocytes in the second white blood cell histogram is subtracted from the counting result (that is, the counting result obtained by multiplying the classification result of the third type of white blood cells by the counting result of white blood cells in the second white blood cell histogram determined as single-peak) of the third type of white blood cells in the first white blood cell histogram after the at least three-classification, to obtain a counting result of the third type of white blood cells in the blood sample; or the classification result of eosinophil granulocytes in the second white blood cell histogram is subtracted from the classification result of the third type of white blood cells in the first white blood cell histogram after the at least three-classification, to obtain a final classification result NEU % of the third type of white blood cells in the blood sample, and then the final classification result NEU % of the third type of white blood cells is multiplied by the counting result WBC2 of white blood cells to obtain a final counting result NEU# of the third type of white blood cells; a counting result EOS# of eosinophil granulocytes is a product of the classification result EOS2% of eosinophil granulocytes in the second white blood cell histogram and the counting result WBC2 of white blood cells in the second white blood cell histogram.

For example, a final five-classification result of white blood cells in the blood sample is shown in Table 2. A final counting result LYM# of the first type of white blood cells, lymphocytes, is a product of the classification result LYM1% of lymphocytes in the first white blood cell histogram and the counting result WBC2 of white blood cells in the second white blood cell histogram; a final counting result MON# of the second type of white blood cells, monocytes, is a product of the classification result MON1% of monocytes in the first white blood cell histogram and the counting result WBC2 of white blood cells in the second white blood cell histogram; and finally, a counting result of eosinophil granulocytes and a counting result of basophil granulocytes in the second white blood cell histogram are subtracted from a counting result (that is, a counting result obtained by multiplying the classification result of the third type of white blood cells by the counting result of white blood cells in the second white blood cell histogram determined as single-peak) of the third type of white blood cells in the first white blood cell histogram after the at least three-classification, to obtain a counting result of the third type of white blood cells in the blood sample; or a classification result of eosinophil granulocytes and a classification result of basophil granulocytes in the second white blood cell histogram are subtracted from the classification result of the third type of white blood cells in the first white blood cell histogram after the at least three-classification, to obtain a final classification result NEU % of the third type of white blood cells in the blood sample, and then the final classification result NEU % of the third type of white blood cells is multiplied by the counting result WBC2 of white blood cells to obtain a final counting result NEU# of the third type of white blood cells; a counting result EOS# of eosinophil granulocytes is a product of the classification result EOS2% of eosinophil granulocytes in the second white blood cell histogram and the counting result WBC2 of white blood cells in the second white blood cell histogram; a counting result BASO# of basophil granulocytes is a product of the classification result BASO % of basophil granulocytes in the second white blood cell histogram and the counting result WBC2 of white blood cells in the second white blood cell histogram.

Finally, the classification result of the first type of white blood cells and the classification result of the second type of white blood cells in the first white blood cell histogram after the at least three-classification are respectively used as a classification result of the first type of white blood cells and a classification result of the second type of white blood cells in the blood sample. Finally, a counting result of the first type of white blood cells and a counting result of the second type of white blood cells in the first white blood cell histogram after the at least three-classification are respectively used as a counting result of the first type of white blood cells and a counting result of the second type of white blood cells in the blood sample.

Figure 15:
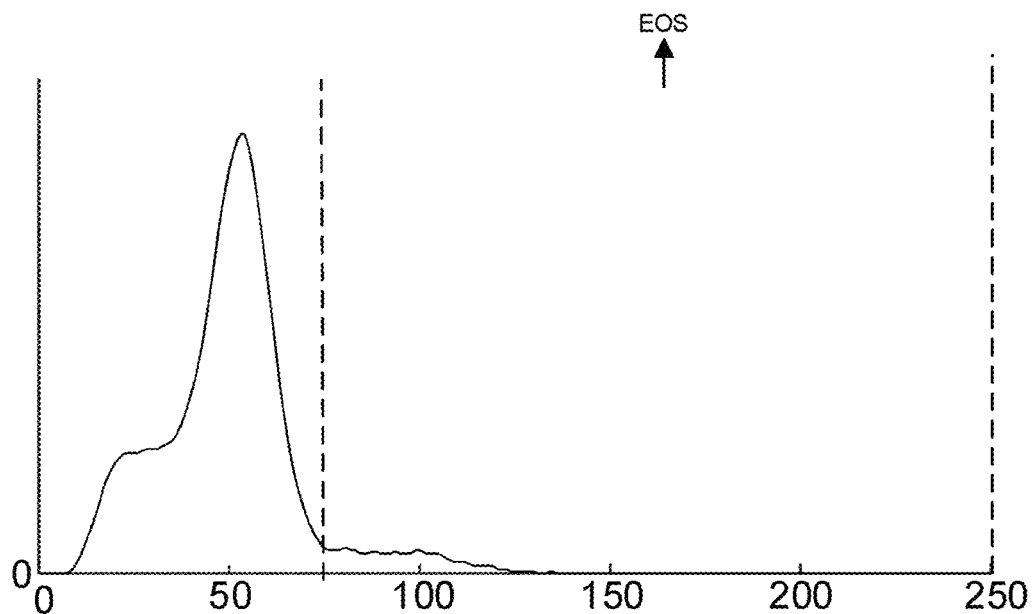
FIG. 15 is a schematic diagram of classification of a second white blood cell histogram having one peak in still another embodiment of the disclosure.
Figure 16:
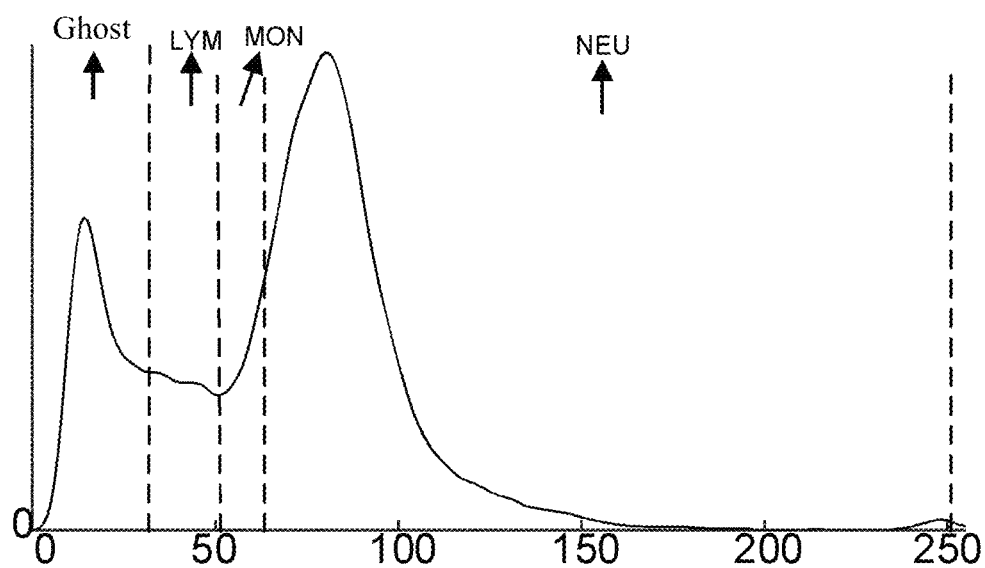
FIG. 16 is a schematic diagram of three-classification of a first white blood cell histogram in another embodiment of the disclosure.

In the specific examples shown in FIGS. 15 and 16, in the second white blood cell histogram obtained based on the blood sample treated with the second hemolytic agent as shown in FIG. 15, it is determined that the second white blood cell histogram is single-peak, and in this case, the obtained white blood cell counting result WBC2 of the second white blood cell histogram is 10.6, and the eosinophil granulocyte Eos % of the second white blood cell histogram obtained according to the method described above is 7.1%; and a three-classification is performed on the first white blood cell histogram as shown in FIG. 16, and the classification result thereof is as shown in Table 3 below:

TABLE 3

| Sample 1 | One-time count |
|---|---|
| WBC1 | 13.2 |
| LYM1% | 21.7 |
| MON1% | 6.9 |
| NEU1% | 71.4 |

Then, according to the method of the foregoing embodiments and the rules in Table 1, the counting result and classification result of the white blood cells in the blood sample can be finally obtained, which are as shown in Table 4:

TABLE 4

| Sample 1 | Counting and classification results | Reference values |
|---|---|---|
| WBC | 10.6 | 10.97 |
| LYM % | 21.7 | 16.5 |
| MON % | 6.9 | 10.8 |
| NEU % | 64.3 | 65.0 |
| EOS % | 7.1 | 7.3 |

It can be seen from Table 4 that when the peak type of the second white blood cell histogram is single-peak, the counting result and classification result obtained by using a classification and counting method of combining the second white blood cell histogram and the first white blood cell histogram are very close to reference values (and actual values). Therefore, it can be seen therefrom that the method can significantly improve the accuracy of counting and classification of white blood cells.

In conclusion, when the peak type of the second white blood cell histogram is single-peak, white blood cell classification and counting are performed by combining a classification result and a counting result of the second white blood cell histogram and a classification result of the first white blood cell histogram. When the peak type of the second white blood cell histogram is single-peak, particle populations of white blood cells of the second white blood cell histogram are distributed close to each other and cannot be easily classified, but the second white blood cell histogram is less affected by ghosts, and therefore the counting result of the second white blood cell histogram is more accurate than that of the first white blood cell histogram. Since the first white blood cell histogram has two peaks, particle populations of white blood cells of the first white blood cell histogram are distributed away from each other and can be easily classified. Therefore, classification and counting of the white blood cells are performed by combining a classification result and a counting result of the second white blood cell histogram determined as single-peak and a classification result of the first white blood cell histogram, such that more accurate classification and counting results of the white blood cells can be obtained. Therefore, the method of the embodiments of the disclosure can improve the accuracy of counting and classification of white blood cells.

It may be understood that when a four-classification is performed on white blood cells in the present application, neutrophil granulocytes are usually distinguished from eosinophil granulocytes or basophil granulocytes on the basis of a three-classification. For example, the white blood cells are classified into lymphocytes, monocytes, neutrophil granulocytes, and eosinophil granulocytes. In this case, basophil granulocytes are classified into the eosinophil granulocytes. When the white blood cells are classified into lymphocytes, monocytes, neutrophil granulocytes and basophil granulocytes, eosinophil granulocytes are classified into the neutrophil granulocytes, and when a report is output, the number of neutrophil granulocytes, and the total number of neutrophil granulocytes and eosinophil granulocytes, or the total number of granulocytes may be shown. That is, the neutrophil granulocytes and the eosinophil granulocytes are not counted separately in this case.

Figure 17:
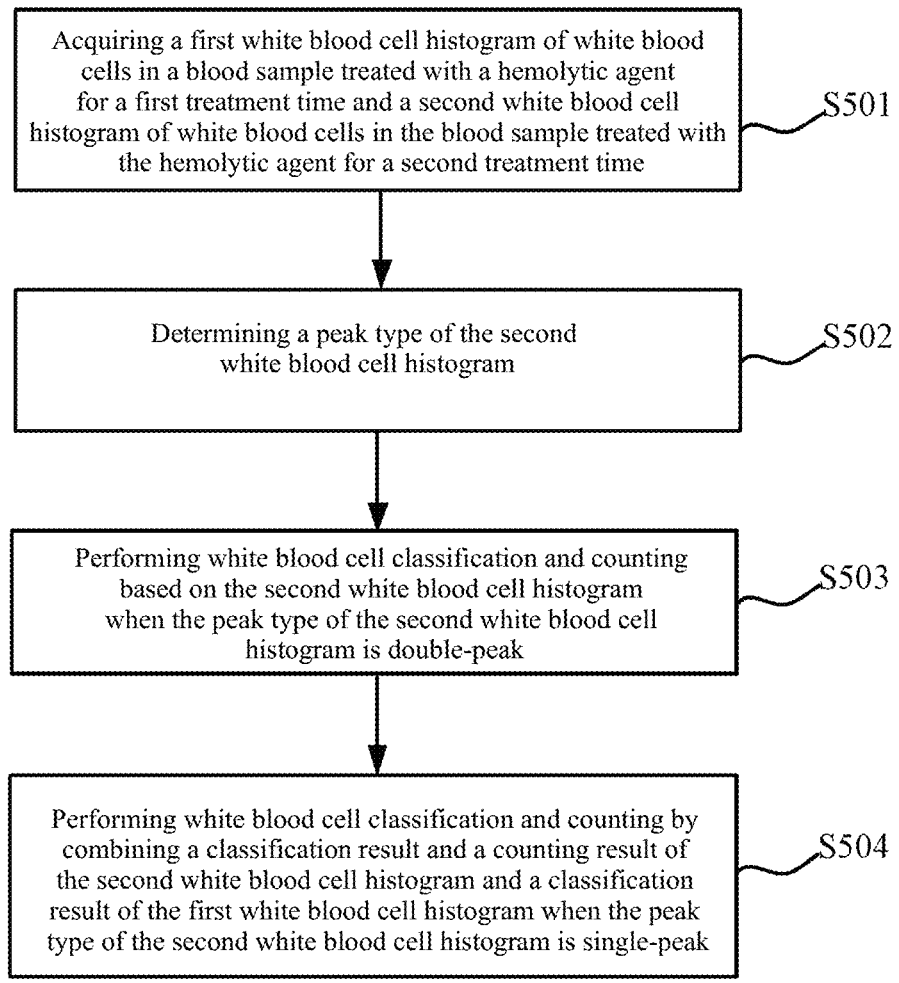
FIG. 17 is a flowchart of a method for counting and classifying white blood cells in still another embodiment of the disclosure.

In another embodiment, as shown in FIG. 17, a method for classifying and counting white blood cells in the embodiment of the disclosure comprises steps S501 to S504 as follows. In step S501, a first white blood cell histogram of white blood cells in a blood sample treated with a hemolytic agent for a first treatment time is acquired and a second white blood cell histogram of white blood cells in the blood sample treated with the hemolytic agent for a second treatment time is acquired, wherein the second treatment time is longer than the first treatment time, a ghost value in the second white blood cell histogram is less than a ghost value in the first white blood cell histogram, and the ghost value in the second white blood cell histogram is less than a ghost value threshold.

In step S501, the first white blood cell histogram of white blood cells in the blood sample treated with the hemolytic agent for the first treatment time is acquired and the second white blood cell histogram of white blood cells in the blood sample treated with the hemolytic agent for the second treatment time is acquired, wherein the second treatment time is longer than the first treatment time.

The first treatment time and the second treatment time may be properly set according to actual reaction conditions, etc. For example, the first treatment time may be zero, or may be a treatment time which is set greater than 0 based on priori experiences. The first treatment time is required to ensure that: there are ghosts in the first white blood cell histogram of white blood cells in the blood sample treated with the hemolytic agent for the first treatment time, a ghost value is greater than or equal to a ghost value threshold, the presence of the ghosts will affect the accuracy of the counting result of white blood cells, and the obtained first white blood cell histogram has two peaks. The second treatment time may be the first treatment time for the hemolytic agent plus a treatment time until a predetermined second treatment time, and then the second white blood cell histogram is generated. In this case, ghosts in the blood sample are significantly reduced or even disappear compared with the ghosts in the blood sample treated for the first treatment time. The second treatment time is required to ensure that: a ghost value in the obtained second white blood cell histogram is less than the ghost value in the first white blood cell histogram, and the ghost value in the second white blood cell histogram is less than the ghost value threshold.

In this embodiment, it can be ensured that a sufficient amount of hemolytic agent is added. The amount of the hemolytic agent is required to ensure that there are few ghosts in the blood sample treated for the second treatment time, such that the generated second white blood cell histogram meets the following requirements: the ghost value in the second white blood cell histogram is less than the ghost value in the first white blood cell histogram, and the ghost value in the second white blood cell histogram is less than the ghost value threshold.

The hemolytic agent can lyse all red blood cells only after a specific treatment time. Within the relatively short first treatment time, only some red blood cells are lysed, and at this time, there are a relatively large number of ghosts in the blood sample, and the first white blood cell histogram can thus be obtained. With the increase of the treatment time and until the second treatment time, more red blood cells are lysed, and ghosts in the blood sample are reduced at this time, and the second white blood cell histogram can thus be obtained.

Subsequently, in step S502, a peak type of the second white blood cell histogram is determined. In step S503, white blood cell classification and counting are performed on the basis of the second white blood cell histogram when the peak type of the second white blood cell histogram is double-peak. In step S504, white blood cell classification and counting are performed by combining a classification result and a counting result of the second white blood cell histogram and a classification result of the first white blood cell histogram when the peak type of the second white blood cell histogram is single-peak.

Reference may be made to the description of steps S402 to S404 in the foregoing embodiments for the description of steps S502 to S504 in this embodiment, which will not be repeated herein to avoid repetition. According to the method in this embodiment of the disclosure, the hemolytic agent needs to be added only once, and by adjusting the treatment time, a first white blood cell histogram and a second white blood cell histogram can be obtained. Therefore, when the peak type of the second white blood cell histogram is single-peak, white blood cell classification and counting are performed by combining a classification result and a counting result of the second white blood cell histogram and a classification result of the first white blood cell histogram. When the peak type of the second white blood cell histogram is single-peak, particle populations of white blood cells of the second white blood cell histogram are distributed close to each other and cannot be easily classified, but the second white blood cell histogram is less affected by ghosts, and therefore the counting result of the second white blood cell histogram is more accurate than that of the first white blood cell histogram. Since the first white blood cell histogram has two peaks, particle populations of white blood cells of the first white blood cell histogram are distributed away from each other and can be easily classified. Therefore, classification and counting of the white blood cells are performed by combining a classification result and a counting result of the second white blood cell histogram determined as single-peak and a classification result of the first white blood cell histogram, such that more accurate classification and counting results of the white blood cells can be obtained. When the second white blood cell histogram is double-peak, accurate classification and counting results of white blood cells can also be obtained by directly performing white blood cell classification and counting on the basis of the second white blood cell histogram. Therefore, the method of the embodiments of the disclosure can improve the accuracy of counting and classification of white blood cells.

An exemplary electronic device 150 for implementing a method for classifying and counting white blood cells according to an embodiment of the disclosure will be described below with reference to FIG. 18.

Figure 18:
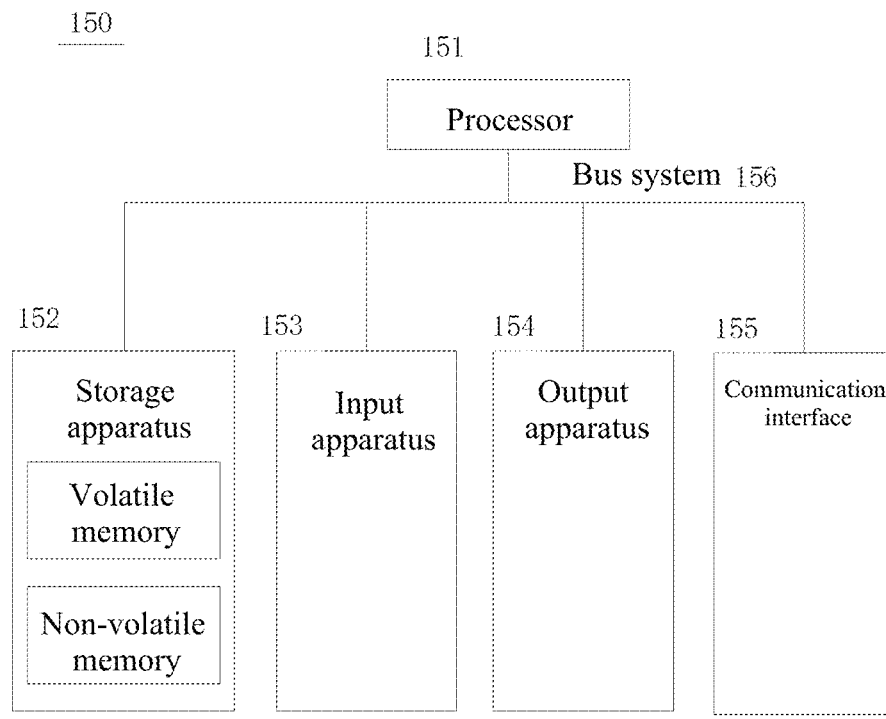
FIG. 18 is a schematic block diagram of an exemplary electronic device for implementing a method and an apparatus for classifying and counting white blood cells according to an embodiment of the disclosure.

In an example, as shown in FIG. 18, the electronic device 150 may comprise one or more processors 151, one or more storage apparatuses 152, an input apparatus 153, an output apparatus 154, and a communication interface 155. These components are interconnected by using a bus system 156 and/or other forms of connection mechanism (not shown). It should be noted that the components and structure of the electronic device 150 shown in FIG. 18 are merely exemplary and not restrictive, and the electronic device may also have other components and structures as required.

The processor 151 may be a central processing unit (CPU), a graphics processing unit (GPU), an application specific integrated circuit (ASIC), a field programmable gate array (FPGA), or other forms of processing unit that has a data processing capability and/or an instruction execution capability, and the processor can control other components in a white blood cell classification and counting apparatus to perform desired functions. The processor can execute programs and/or instructions stored in the storage apparatus to perform the method for classifying and counting white blood cells described herein. For example, the processor 151 may comprise one or more embedded processors, processor cores, microprocessors, logic circuits, hardware finite state machines (FSM), digital signal processors (DSP), or a combination thereof.

The storage apparatus 152 may comprise one or more computer program products, and the computer program product may comprise various forms of computer-readable storage media, such as a volatile memory and/or a non-volatile memory. The volatile memory may, for example, comprise a random-access memory (RAM) and/or a cache memory (cache). The non-volatile memory may, for example, comprise a read-only memory (ROM), a hard disk, a flash memory, etc. The computer-readable storage medium may have stored thereon one or more computer program instructions, which can be run by the processor 151 to implement the functions and/or other desired functions (implemented by the processor) in the embodiments of the disclosure descended herein. The computer-readable storage medium may also store various application programs and various data, such as various data used and/or generated by the application programs.

The input apparatus 153 may be an apparatus used by a user to enter an instruction (for example, in the method for classifying and counting white blood cells according to an embodiment of the disclosure described herein, the user may enter a parameter such as a predetermined volume during the demarcation of a demarcation line), and may comprise one or more of a keyboard, a mouse, a microphone, a touchscreen, etc. In addition, the input apparatus 153 may also be any interface for receiving information.

The output apparatus 154 may output various information (such as an image or sound) to the outside (such as a user), and may comprise one or more of a display (such as to display, to the user, a list of parameters of a white blood cell classification and counting apparatus, white blood cell classification and counting results, and white blood cell classification histograms, etc.), a speaker, etc.

The communication interface 155 is used for communication between the electronic device 150 and other devices, including wired or wireless communication. The electronic device 150 can access a wireless network which is based on a communications standard, such as WiFi, 2G, 3G, 4G, 5G, or a combination thereof. In an exemplary embodiment, the communication interface 155 further comprises a near-field communication (NFC) module to facilitate short-range communication. For example, the NFC module may be implemented on the basis of a radio frequency identification (RFID) technology, an infrared data association (IrDA) technology, an ultra-wideband (UWB) technology, a Bluetooth (BT) technology, and other technologies.

Exemplarily, the exemplary electronic device for implementing the method for classifying and counting white blood cells according to an embodiment of the disclosure may be implemented as a terminal, such as a desktop computer and a tablet computer, or a hematology analyzer including these terminals, etc.

Additionally, an embodiment of the disclosure further provides a computer-readable storage medium having a computer program stored thereon. The computer-readable storage medium may have stored thereon one or more computer program instructions, and a processor can run the program instructions stored in the storage apparatus so as to implement the functions and/or other desired functions (implemented by the processor) in the embodiments of the disclosure descended herein, such as to perform the corresponding steps of a method for classifying and counting white blood cells according to an embodiment of the disclosure. The computer-readable storage medium may also store various application programs and various data, such as various data used and/or generated by the application programs.

For example, the computer-readable storage medium may comprise, for example, a memory card of a smartphone, a storage component of a tablet computer, a hard disk of a personal computer, a read-only memory (ROM), an erasable programmable read-only memory (EPROM), a portable compact disk read-only memory (CD-ROM), a USB memory, or any combination of the above storage media.

Figure 19:
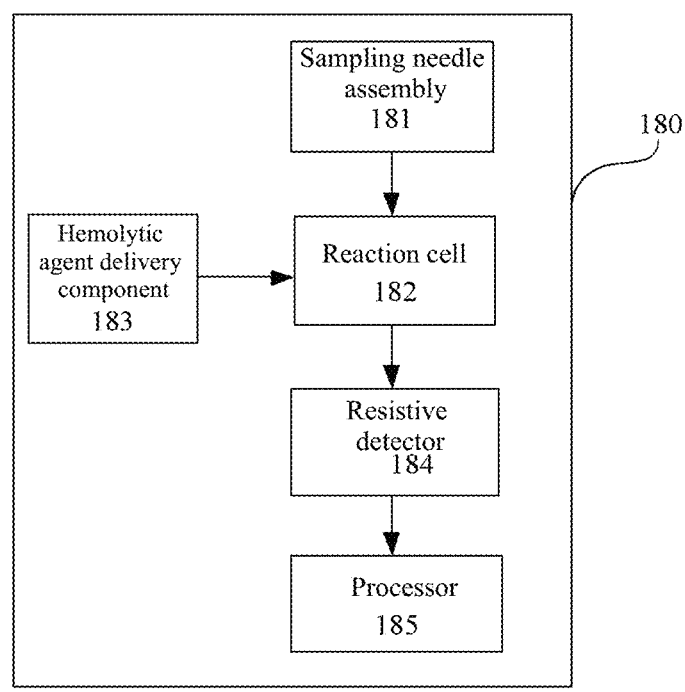
FIG. 19 is a schematic block diagram of a hematology analyzer in one embodiment of the disclosure.

A blood sample analyzer provided in another aspect of the disclosure will be described below with reference to FIG. 19. FIG. 19 is a schematic block diagram of a hematology analyzer in one embodiment of the disclosure.

The hematology analyzer is configured to perform various types of analysis on blood compositions, for example, counting and classifying of white blood cells in blood, measuring concentration of hemoglobin (HGB) in red blood cells, counting of platelets, etc.

As shown in FIG. 19, the blood sample analyzer comprises at least one reaction cell 182 and a sampling needle assembly 181. The reaction cell 182 is configured to prepare a blood sample from a blood sample to be tested, and the sampling needle assembly 181 is configured to discharge the blood sample to be analyzed to the reaction cell 182. In another embodiment, the sampling needle assembly 181 may also be implemented in other ways than a sampling needle.

In an example, the hematology analyzer further comprises a reagent storage apparatus (not shown). The reagent storage apparatus is connected to the reaction cell 182 and is configured to provide the reaction cell 182 with reagents for preparing the blood sample, such as a hemolytic agent and a diluent. The number of the reagent storage apparatuses is properly set according to types of the reagents. For example, the reagent storage apparatus comprises a storage apparatus for storing a hemolytic agent and a storage apparatus for storing a diluent, wherein the storage apparatus for storing a hemolytic agent may also be divided into one or more storage apparatuses according to types of hemolytic agents, for example, a storage apparatus for storing a first hemolytic agent and a storage apparatus for storing a second hemolytic agent. Only one hemolytic agent storage apparatus may be provided when the first hemolytic agent and the second hemolytic agent are a same hemolytic agent.

In an example, the hematology analyzer 180 further comprises a hemolytic agent delivery component 183, which is configured to deliver a hemolytic agent to the reaction cell 182, the hemolytic agent comprising a first hemolytic agent and a second hemolytic agent. Exemplarily, the hemolytic agent delivery component 183 may be connected to the hemolytic agent storage apparatus and the reaction cell, so as to deliver a corresponding hemolytic agent to the reaction cell 182. After reagents are injected into a reaction apparatus, the blood sample, the hemolytic agent, the diluting liquid, etc. are mixed in the reaction cell 182 to prepare a blood sample for testing white blood cells.

The hematology analyzer 180 further comprises a transfer apparatus (not shown). The transfer apparatus is configured to transfer a sample liquid in the reaction cell 182 to a resistive detector 184. In this embodiment, the transfer apparatus comprises a syringe and a transfer pipeline in communication with the syringe, and the syringe, a sample liquid outlet of the reaction cell, and an inlet of the detection apparatus are in communication through the transfer pipeline. There may be a plurality of syringes, and each syringe makes aspiration and discharge actions under the control of a control apparatus.

In an example, as shown in FIG. 19, the hematology analyzer 180 further comprises a resistive detector 184. The resistive detector 184 is configured to detect white blood cells in the blood sample treated with the first hemolytic agent and generate first signals, such as pulse signals, and to detect white blood cells in the blood sample treated with the second hemolytic agent and generate second signals, such as pulse signals. For example, the resistive detector 184 is configured to detect white blood cells in the blood sample, and output the pulse signals when the white blood cells pass through a detection aperture in the resistive detector 184, wherein the number of the pulse signals is proportional to the number of cells, and an amplitude of each pulse signal is proportional to a volume of a cell, from which number and volume values of blood cell particles in the blood can be obtained. The resistive detector 184 is configured to detect the blood sample prepared in the reaction cell.

In an example, the structure of the resistive detector 184 may comprise a counting cell (not shown) and a pulse sensor (not shown). The counting cell and the reaction cell may be a same apparatus or different apparatuses. Optionally, the pulse sensor may comprise an aperture tube, and the aperture tube is provided with a detection aperture. Optionally, a diameter of the detection aperture is less than 100 micrometers, and a thickness thereof ranges from 60 micrometers to 90 micrometers, such as about 75 micrometers. The counting cell is filled with a conductive solvent, and is divided into a front cell and a rear cell by the detection aperture. The front cell and the rear cell are provided with a positive electrode and a negative electrode respectively, wherein the positive electrode and the negative electrode are connected to one end of a constant-current source; and the electrode provided in the front cell, the conductive solvent, the electrode provided in the rear cell, and the constant-current source together constitute a serially connected closed loop. After being powered on, the electrodes located at two sides of the aperture tube produce a steady current, and a cell diluting suspension flows from the outside of the aperture tube to the inside of the aperture tube through the detection aperture, such that a resistance in a sensing region of the aperture is increased, thereby resulting in a change in a transient voltage so as to form pulse signals, wherein an amplitude of each pulse signal is proportional to a volume size of a cell, and the number of pulses is proportional to the number of cells, from which number and volume values of blood cells in the blood sample can be obtained, and different types of cells can be distinguished according to volume distribution.

In another embodiment, the sampling needle assembly is configured to discharge a blood sample to be analyzed to the reaction cell; the hemolytic agent delivery component is configured to deliver a hemolytic agent to the reaction cell; and the resistive detector is configured to detect white blood cells in the blood sample treated with a hemolytic agent for a first treatment time and generate first signals, and to detect white blood cells in the blood sample treated with the hemolytic agent for a second treatment time and generate second signals, wherein the second treatment time is longer than the first treatment time.

In an example, the hematology analyzer 180 further comprises one or more processors 185, which operate together or separately and are configured to acquire a first white blood cell histogram on the basis of the first signals and acquire a second white blood cell histogram on the basis of the second signals, wherein a ghost value in the second white blood cell histogram is less than a ghost value in the first white blood cell histogram, and the ghost value in the second white blood cell histogram is less than a ghost value threshold. For example, during each time of detection, the processor 185 receives signals output by the resistive detector 184, such as first signals and second signals, and analyzes the first signals and the second signals, so as to obtain the first white blood cell histogram and the second white blood cell histogram on the basis of the first signals and the second signals.

In an embodiment, the hematology analyzer 180 comprises one or more processors 185 and one or more storage apparatuses (not shown). The one or more processors operate together or separately. The storage apparatus stores a program for implementing the corresponding steps in the method for classifying and counting white blood cells according to the embodiments of the disclosure. The processor is configured to run the program stored in the storage apparatus to perform the corresponding steps of the method for classifying and counting white blood cells according to the embodiments of the disclosure.

In an embodiment of the disclosure, the program, when run by the processor, causes the hematology analyzer 180 to perform the following steps:

acquiring a first white blood cell histogram on the basis of the first signals and acquiring a second white blood cell histogram on the basis of the second signals, wherein a ghost value in the second white blood cell histogram is less than a ghost value in the first white blood cell histogram, and the ghost value in the second white blood cell histogram is less than a ghost value threshold;

performing white blood cell classification and counting on the basis of the second white blood cell histogram when the peak type of the second white blood cell histogram is double-peak; and performing white blood cell classification and counting by combining a classification result and a counting result of the second white blood cell histogram and a classification result of the first white blood cell histogram when the peak type of the second white blood cell histogram is single-peak.

In an example, the sampling needle assembly is configured to discharge the blood sample to be analyzed to the reaction cell for the first time to perform a first measurement, and to discharge the blood sample to be analyzed to the reaction cell for the second time to perform a second measurement. The hemolytic agent delivery component is configured to: deliver the first hemolytic agent into the reaction cell to complete the first measurement and generate the first white blood cell histogram; and deliver the second hemolytic agent into the reaction cell to complete the second measurement and generate the second white blood cell histogram.

In another example, the sampling needle assembly 181 is configured to discharge the blood sample to be analyzed to the reaction cell 182. The hemolytic agent delivery component is configured to: first deliver the first hemolytic agent into the blood sample in the reaction cell to obtain a test solution to complete the first measurement and obtain the first white blood cell histogram; and then deliver the second hemolytic agent into the test solution in the reaction cell to complete the second measurement and obtain the second white blood cell histogram.

In other examples, the hemolytic agent delivery component is configured to: sequentially deliver hemolytic agents into the same blood sample in the reaction cell at least three times, with the hemolytic agent added each time comprising at least one of the first hemolytic agent and the second hemolytic agent. The resistive detector is configured to: detect the white blood cells in the blood sample and generate corresponding signals each time after the hemolytic agent delivery component delivers the first hemolytic agent and/or the second hemolytic agent. The processor is configured to: generate corresponding white blood cell histograms on the basis of the corresponding signals, and select, from the corresponding white blood cell histograms, two successively generated white blood cell histograms as the first white blood cell histogram and the second white blood cell histogram, respectively.

In an embodiment, the program, when run by the processor, causes the hematology analyzer 180 to perform the following steps: performing classification and counting on the second white blood cell histogram determined as single-peak, to obtain a counting result of white blood cells and a classification result of eosinophil granulocytes and/or a classification result of basophil granulocytes in the white blood cells; obtaining at least four-classification result according to the classification result of the second white blood cell histogram and a classification result of the first white blood cell histogram after at least three-classification; and calculating a counting result of each type of white blood cells in the blood sample on the basis of the at least four-classification result and the counting result of white blood cells.

The first white blood cell histogram after the at least three-classification comprises a first type of white blood cells, a second type of white blood cells, and a third type of white blood cells. In an embodiment, the program, when run by the processor, causes the hematology analyzer 180 to perform the following steps: determining a counting result of eosinophil granulocytes and/or a counting result of basophil granulocytes in the second white blood cell histogram as a counting result of eosinophil granulocytes and/or a counting result of basophil granulocytes in the blood sample; subtracting the counting result of eosinophil granulocytes and/or the counting result of basophil granulocytes in the second white blood cell histogram from a counting result of the third type of white blood cells in the first white blood cell histogram after the at least three-classification, to obtain a counting result of the third type of white blood cells in the blood sample; and determining a counting result of the first type of white blood cells and a counting result of the second type of white blood cells in the first white blood cell histogram after the at least three-classification as a counting result of the first type of white blood cells and a counting result of the second type of white blood cells in the blood sample, respectively.

In an embodiment, the classification result of each type of white blood cells in the first white blood cell histogram is a proportion of the type of white blood cells in the first white blood cell histogram with a ghost region removed; and/or the classification result of eosinophil granulocytes is a proportion of a region of the eosinophil granulocytes in the second white blood cell histogram; the classification result of basophil granulocytes is a proportion of the eosinophil granulocytes in the second white blood cell histogram.

In an embodiment, the hematology analyzer further comprises a test mode selection module configured to select a predetermined test mode according to an animal type to which the blood sample belongs, wherein the hemolytic agent delivery component delivers a corresponding hemolytic agent to the reaction cell for reaction according to the selected test mode.

In an embodiment, the program, when run by the processor, causes the hematology analyzer 180 to perform the related steps of the method for classifying and counting white blood cells described in the foregoing embodiments.

The complete hematology analyzer may further comprise other components, which will not be described in detail herein.

In conclusion, according to the method for classifying and counting white blood cells, the hematology analyzer, and the storage medium in the embodiments of the disclosure, a first white blood cell histogram and a second white blood cell histogram of white blood cells in blood samples respectively treated with a first hemolytic agent and a second hemolytic agent are acquired, and a manner of counting and classification of white blood cells is determined according to a peak type of the second white blood cell histogram. When the peak type of the second white blood cell histogram is double-peak and a ghost value in the second white blood cell histogram is less than a ghost value threshold, ghosts hardly interfere with the counting based on the second white blood cell histogram. In addition, since the second white blood cell histogram is double-peak and regions of particle populations of various types of white blood cells in the second white blood cell histogram are distributed away from each other, accurate classification and counting results of white blood cells in blood can be obtained directly by means of counting based on the second white blood cell histogram. When the peak type of the second white blood cell histogram is single-peak, white blood cell classification and counting are performed by combining a classification result and a counting result of the second white blood cell histogram and a classification result of the first white blood cell histogram. When the peak type of the second white blood cell histogram is single-peak, particle populations of white blood cells of the second white blood cell histogram are distributed close to each other and cannot be easily classified, but the second white blood cell histogram is less affected by ghosts, and therefore the counting result of the second white blood cell histogram is more accurate than that of the first white blood cell histogram. Since the first white blood cell histogram has two peaks, particle populations of white blood cells of the first white blood cell histogram are distributed away from each other and can be easily classified. Therefore, classification and counting of the white blood cells are performed by combining a classification result and a counting result of the second white blood cell histogram determined as single-peak and a classification result of the first white blood cell histogram, such that more accurate classification and counting results of the white blood cells can be obtained. Therefore, the method of the embodiments of the disclosure can improve the accuracy of counting and classification of white blood cells. Therefore, the counting and classification results are used to more truly reflect the actual condition of the tested blood sample, such that a physician and other personnel properly determine the health condition of a subject of the blood sample on the basis of the results, so as to make a reasonable medical diagnosis, etc.

While example embodiments have been described herein with reference to the accompanying drawings, it should be understood that the above example embodiments are merely illustrative and are not intended to limit the scope of the disclosure thereto. Those of ordinary skill in the art may make various changes and modifications therein without departing from the scope and spirit of the disclosure. All such changes and modifications are intended to be included in the scope of the disclosure as claimed in the appended claims.

A person of ordinary skill in the art may be aware that, in combination with the examples described in the embodiments disclosed in this specification, units and algorithm steps may be implemented by using electronic hardware or a combination of computer software and electronic hardware. Whether the functions are performed by hardware or software depends on particular applications and design constraint conditions of the technical solutions. Those skilled in the art could use different methods to implement the described functions for each particular application, but such implementation should not be considered to be beyond the scope of the disclosure.

In several embodiments provided in the present application, it should be understood that the disclosed devices and methods may be implemented in other ways. For example, the device embodiments described above are merely exemplary. For example, the division of units is merely a logical function division. In actual implementations, there may be other division methods. For example, a plurality of units or components may be combined or integrated into another device, or some features may be omitted or not implemented.

A large number of specific details are explained in this specification provided herein. However, it can be understood that the embodiments of the disclosure can be practiced without these specific details. In some instances, well-known methods, structures, and technologies are not shown in detail, so as not to obscure the understanding of this description.

Similarly, it should be understood that in order to simplify the disclosure and help to understand one or more of various aspects of the disclosure, in the description of the exemplary embodiments of the disclosure, various features of the disclosure are sometimes together grouped into an individual embodiment, figure or description thereof. However, the method of the disclosure should not be construed as reflecting the following intention: namely, the disclosure set forth requires more features than those explicitly stated in each claim. More precisely, as reflected by the corresponding claims, the inventive point thereof lies in that features that are fewer than all the features of an individual embodiment disclosed may be used to solve the corresponding technical problem. Therefore, the claims in accordance with the particular embodiments are thereby explicitly incorporated into the particular embodiments, wherein each claim itself serves as an individual embodiment of the disclosure.

Those skilled in the art should understand that, in addition to the case where features are mutually exclusive, any combination may be used to combine all the features disclosed in this specification (along with the appended claims, abstract, and drawings) and all the processes or units of any of methods or devices as disclosed. Unless explicitly stated otherwise, each feature disclosed in this specification (along with the appended claims, abstract, and drawings) may be replaced by an alternative feature that provides the same, equivalent, or similar object.

Furthermore, those skilled in the art should understand that although some of the embodiments described herein comprise some but not other features included in other embodiments, combinations of features of different embodiments are meant to be within the scope of the disclosure, and form different embodiments. For example, in the claims, any one of the embodiments set forth thereby can be used in any combination.

Various embodiments regarding components in the disclosure may be implemented in hardware, or implemented by software modules running on one or more processors, or implemented in a combination thereof. It should be understood for those skilled in the art that a microprocessor or a digital signal processor (DSP) may be used in practice to implement some or all of the functions of some modules according to the embodiments of the disclosure. The disclosure may further be implemented as an apparatus program (e.g. a computer program and a computer program product) for executing some or all of the methods described herein. Such a program for implementing the disclosure may be stored on a computer-readable medium, or may be in the form of one or more signals. Such a signal may be downloaded from an Internet website, or provided on a carrier signal, or provided in any other form.

It should be noted that the description of the disclosure made in the above-mentioned embodiments is not to limit the disclosure, and those skilled in the art may design alternative embodiments without departing from the scope of the appended claims. In the claims, any reference signs placed between parentheses should not be construed as limitation on the claims. The disclosure may be implemented by means of hardware comprising several different elements and by means of an appropriately programmed computer. In unit claims listing several apparatuses, several of these apparatuses may be specifically embodied by one and the same item of hardware. The use of the terms "first", "second", "third", etc. does not indicate any order. These terms may be interpreted as names.

The invention claimed is:

1. A method for classifying and counting white blood cells, comprising:
   acquiring a first white blood cell histogram of white blood cells in a blood sample treated with a first hemolytic agent and a second white blood cell histogram of the white blood cells in the blood sample treated with a second hemolytic agent, wherein a ghost value in the second white blood cell histogram is less than a ghost value in the first white blood cell histogram, and the ghost value in the second white blood cell histogram is less than a ghost value threshold;
   determining a peak type of the second white blood cell histogram;
   performing white blood cell classification and counting based on the second white blood cell histogram when the peak type of the second white blood cell histogram is double-peak; and
   performing white blood cell classification and counting by combining a classification result and a counting result of the second white blood cell histogram and a classification result of the first white blood cell histogram when the peak type of the second white blood cell histogram is single-peak.

2. The method of claim 1, wherein the first hemolytic agent and the second hemolytic agent are a same hemolytic agent.

3. The method of claim 1, wherein a dose of the second hemolytic agent used for treating the blood sample is greater than a dose of the first hemolytic agent used for treating the blood sample.

4. The method of claim 1, wherein the step of acquiring a first white blood cell histogram of white blood cells in a blood sample treated with a first hemolytic agent and a second white blood cell histogram of the white blood cells in the blood sample treated with a second hemolytic agent comprises:
   first adding the first hemolytic agent to the blood sample to obtain a test solution, so as to obtain the first white blood cell histogram, and
   then adding the second hemolytic agent to the test solution, so as to obtain the second white blood cell histogram;
   or
   sequentially adding a hemolytic agent to the same blood sample at least three times, wherein the hemolytic agent added each time comprises at least one of the first hemolytic agent and the second hemolytic agent, and a corresponding white blood cell histogram is generated after each addition of the first hemolytic agent and/or the second hemolytic agent, and
   selecting two successively generated white blood cell histograms as the first white blood cell histogram and the second white blood cell histogram respectively.

5. The method of claim 1, further comprising performing at least three-classification on the first white blood cell histogram, to obtain a three-classification result of the first white blood cell histogram, wherein the first white blood cell histogram comprises at least a first type of white blood cells, a second type of white blood cells, and a third type of white blood cells;
- wherein the abscissa of each white blood cell histogram represents cell volume, and the ordinate of each white blood cell histogram represents cell number; and
- wherein the step of performing white blood cell classification and counting by combining a classification result and a counting result of the second white blood cell histogram and a classification result of the first white blood cell histogram comprises:
  - performing classification and counting of white blood cells based on the second white blood cell histogram determined as single-peak, to obtain a counting result of white blood cells and a classification result of eosinophil granulocytes and/or a classification result of basophil granulocytes in the white blood cells;
  - obtaining a four-classification result of white blood cells according to the classification result of the second white blood cell histogram and the three-classification result of the first white blood cell histogram; and
  - calculating a counting result of each type of white blood cells in the blood sample based on the four-classification result of white blood cells and the counting result of white blood cells.

6. The method of claim 5, wherein the step of calculating a counting result of each type of white blood cells in the blood sample based on the four-classification result of white blood cells and the counting result of white blood cells comprises:
- determining the counting result of eosinophil granulocytes and/or the counting result of basophil granulocytes in the second white blood cell histogram as a counting result of eosinophil granulocytes and/or a counting result of basophil granulocytes in the blood sample;
- subtracting the counting result of eosinophil granulocytes and/or the counting result of basophil granulocytes in the second white blood cell histogram from a counting result of the third type of white blood cells in the first white blood cell histogram after the at least three-classification, to obtain a counting result of the third type of white blood cells in the blood sample; and
- determining a counting result of the first type of white blood cells and a counting result of the second type of white blood cells in the first white blood cell histogram after the at least three-classification as a counting result of the first type of white blood cells and a counting result of the second type of white blood cells in the blood sample, respectively.

7. The method of claim 5, wherein the classification result of each of the first type of white blood cells, the second type of white blood cells, and the third type of white blood cells is a proportion of the type of white blood cells in the first white blood cell histogram with a ghost region removed; and/or
- the classification result of eosinophil granulocytes is a proportion of a region of the eosinophil granulocytes in the second white blood cell histogram; and/or
- the classification result of basophil granulocytes is a proportion of a region of the eosinophil granulocytes in the second white blood cell histogram.

8. The method of claim 5, further comprising:
- after determining the peak type of the second white blood cell histogram, if it is determined that the peak type of the second white blood cell histogram is single-peak, and the peak type of the first white blood cell histogram is double-peak, performing the at least three-classification on the first white blood cell histogram.

9. The method of claim 5, wherein the step of performing white blood cell classification and counting by combining a classification result and a counting result of the second white blood cell histogram and a classification result of the first white blood cell histogram when the peak type of the second white blood cell histogram is single-peak comprises:
- determining a peak point of the second white blood cell histogram; and
- searching, from the peak point and in a volume increasing direction, for a first demarcation point on a curve of the second white blood cell histogram, at which a slope is greater than a first threshold slope for the first time, wherein a region in the second white blood cell histogram that has a volume greater than a volume corresponding to the first demarcation point represents eosinophil granulocytes.

10. The method of claim 9, wherein the step of performing white blood cell classification and counting by combining a classification result and a counting result of the second white blood cell histogram and a classification result of the first white blood cell histogram when the peak type of the second white blood cell histogram is single-peak further comprises:
- determining a fourth demarcation line between the eosinophil granulocytes and the basophil granulocytes according to a third demarcation line passing through the first demarcation point, wherein the fourth demarcation line is separated from the third demarcation line by a predetermined volume, and a volume corresponding to the fourth demarcation line is greater than a volume corresponding to the third demarcation line, a region between the third demarcation line and the fourth demarcation line represents eosinophil granulocytes, and a region in the second white blood cell histogram that has a volume greater than the volume corresponding to the fourth demarcation line represents basophil granulocytes.

11. The method of claim 9, wherein the first threshold slope is less than 0.

12. The method of claim 5, wherein the step of performing white blood cell classification and counting by combining a classification result and a counting result of the second white blood cell histogram and a classification result of the first white blood cell histogram when the peak type of the second white blood cell histogram is single-peak further comprises:
- determining a fourth demarcation line from a maximum volume and in a volume decreasing direction, the fourth demarcation line being separated from the maximum volume by a predetermined volume, wherein a region in the second white blood cell histogram that has a volume greater than a volume corresponding to the fourth demarcation line represents the basophil granulocytes.

13. The method of claim 1, wherein the step of determining a peak type of the second white blood cell histogram comprises:
- determining the peak type of the second white blood cell histogram according to a number of peak points in the second white blood cell histogram, wherein if there are two peak points, and a distance between the two peak points is greater than a preset distance, the second white blood cell histogram is double-peak; otherwise, the second white blood cell histogram is single-peak.

14. The method of claim 1, wherein the abscissa of each white blood cell histogram represents cell volume, and the ordinate of each white blood cell histogram represents cell number;
- wherein the step of performing white blood cell classification and counting based on the second white blood cell histogram when the peak type of the second white blood cell histogram is double-peak comprises:
- determining a first demarcation line between a first type of white blood cells and a second type of white blood cells according to a trough point between two peak points in the second white blood cell histogram, wherein a volume of the first type of white blood cells is less than a volume of the second type of white blood cells;
- determining a second demarcation line between the second type of white blood cells and a third type of white blood cells according to the first demarcation line, wherein the second demarcation line is separated from the first demarcation line by a first predetermined volume, and a volume corresponding to the second demarcation line is greater than a volume corresponding to the first demarcation line;
- searching, from a maximum volume of the second white blood cell histogram and in a volume decreasing direction, for a second demarcation point on a curve of the second white blood cell histogram, at which a slope is greater than a second threshold slope for the first time; and
- determining a third demarcation line between the third type of white blood cells and a fourth type of white blood cells based on the second demarcation point.

15. The method of claim 14, wherein the step of performing white blood cell classification and counting based on the second white blood cell histogram when the peak type of the second white blood cell histogram is double-peak further comprises:
- determining a fourth demarcation line between the fourth type of white blood cells and a fifth type of white blood cells according to the third demarcation line, wherein the fourth demarcation line is separated from the third demarcation line by a second predetermined volume, and a volume corresponding to the fourth demarcation line is greater than a volume corresponding to the third demarcation line, and a region in the second white blood cell histogram that has a volume greater than the volume corresponding to the fourth demarcation line represents the fifth type of white blood cells.

16. The method of claim 15, wherein the first type of white blood cells are lymphocytes, the second type of white blood cells are monocytes, the third type of white blood cells are neutrophil granulocytes, the fourth type of white blood cells are eosinophil granulocytes, and the fifth type of white blood cells are basophil granulocytes.

17. The method of claim 1, wherein the first white blood cell histogram and the second white blood cell histogram are both obtained by testing the blood sample based on an electrical impedance method.

18. The method of claim 1, wherein the blood sample is an animal blood sample.

19. A white blood cell classification and counting method, comprising:
- acquiring a first white blood cell histogram of white blood cells in a blood sample treated with a hemolytic agent for a first treatment time and a second white blood cell histogram of white blood cells in the blood sample treated with the hemolytic agent for a second treatment time, wherein the second treatment time is longer than the first treatment time, a ghost value in the second white blood cell histogram is less than a ghost value in the first white blood cell histogram, and the ghost value in the second white blood cell histogram is less than a ghost value threshold;
- determining a peak type of the second white blood cell histogram;
- performing white blood cell classification and counting based on the second white blood cell histogram when the peak type of the second white blood cell histogram is double-peak; and
- performing white blood cell classification and counting by combining a classification result and a counting result of the second white blood cell histogram and a classification result of the first white blood cell histogram when the peak type of the second white blood cell histogram is single-peak.

* * * * *